(12) United States Patent
Su

(10) Patent No.: US 9,403,792 B2
(45) Date of Patent: Aug. 2, 2016

(54) METHODS OF USING PYRUVATE KINASE ACTIVATORS

(75) Inventor: Shin-San M. Su, Newton, MA (US)

(73) Assignee: AGIOS PHARMACEUTICALS, INC, Cambridge, MA (US)

( * ) Notice: Subject to any disclaimer, the term of this patent is extended or adjusted under 35 U.S.C. 154(b) by 128 days.

(21) Appl. No.: 14/115,293

(22) PCT Filed: May 3, 2012

(86) PCT No.: PCT/US2012/036411
§ 371 (c)(1),
(2), (4) Date: Jan. 22, 2014

(87) PCT Pub. No.: WO2012/151450
PCT Pub. Date: Nov. 8, 2012

(65) Prior Publication Data
US 2014/0148444 A1    May 29, 2014

Related U.S. Application Data

(60) Provisional application No. 61/482,167, filed on May 3, 2011.

(51) Int. Cl.
| | | |
|---|---|---|
| A61K 31/535 | (2006.01) | |
| C07D 471/04 | (2006.01) | |
| C07D 319/18 | (2006.01) | |
| A61K 31/4704 | (2006.01) | |
| A61K 31/495 | (2006.01) | |
| A61K 31/496 | (2006.01) | |
| A61K 31/5025 | (2006.01) | |
| A61K 31/551 | (2006.01) | |
| A61K 31/635 | (2006.01) | |
| A01N 1/02 | (2006.01) | |

(52) U.S. Cl.
CPC ............ *C07D 319/18* (2013.01); *A01N 1/0226* (2013.01); *A61K 31/4704* (2013.01); *A61K 31/495* (2013.01); *A61K 31/496* (2013.01); *A61K 31/5025* (2013.01); *A61K 31/551* (2013.01); *A61K 31/635* (2013.01)

(58) Field of Classification Search
CPC ........................... A61K 31/535; C07D 471/04
USPC ....................................... 514/234.2; 544/127
See application file for complete search history.

(56) References Cited

FOREIGN PATENT DOCUMENTS

| WO | 9948490 A1 | 9/1999 |
| WO | 2004110418 A2 | 12/2004 |
| WO | 2007016354 A1 | 2/2007 |
| WO | 2010/042867 A2 | 4/2010 |

OTHER PUBLICATIONS

Boxer, et al. "Evaluation of Substituted N,N'-Diarylsulfonamides as Activators of the Tumor Cell Specific M2 Isoform of Pyruvate Kinase" Journal of Medicinal Chemistry (2010) vol. 53, pp. 1048-1055.

International Search Report and Written Opinion for International Application No. PCT/US2012/036411 dated Oct. 9, 2012.

Jiang et al. "Evaluation of thieno[3,2-b]pyrrole[3,2-d]pyridazinones as activators of the tumor cell specific M2 isoform of pyruvate kinase" Bioorganic & Medicinal Chemistry Letters (2010) vol. 20, pp. 3387-3393.

*Primary Examiner* — Raymond Henley, III
(74) *Attorney, Agent, or Firm* — Lando & Anastasi, LLP

(57) ABSTRACT

Described herein are compounds that activate pyruvate kinase, for use in a method for increasing lifetime of the red blood cells, for regulating 2,3-diphosphoglycerate levels in blood and for treating sickle cell anemia.

42 Claims, No Drawings

METHODS OF USING PYRUVATE KINASE ACTIVATORS

This application is a national stage application under 35 U.S.C. §371 of International Application No. PCT/US2012/036411, filed May 3, 2012, and published as International Publication No. WO 2012/151450 on Nov. 8, 2012, which claims priority from U.S. Ser. No. 61/482,167, filed May 3, 2011. The contents of each of these applications is incorporated herein by reference in its entirety.

Pyruvate kinase deficiency (PKD) is one of the most common enzyme defects in erythrocytes in human due to autosomal recessive mutations of the PKLR gene (Zanella, A., et al., Br J Haematol 2005, 130 (1), 11-25). It is also the most frequent enzyme mutation in the central glycolytic pathway and only second to glucose-6 phosphate dehydrogenase (G6PD) deficiency (Kedar, P., et al., Clin Genet 2009, 75 (2), 157-62) of the hexose monophosphate shunt.

Human erythrocytes are unique in that they anucleate when mature. Immature erytocytes have nuclei but during early erythropoiesis prior to becoming circulating reticulocytes they extrude nuclei as well as other organelles such as mitochondria, endoplasmic reticulum, and golgi apparatus, in order to make room for oxygen-carrying hemoglobin. As a result of lacking mitochondria, mature red blood cells do not utilize any of the oxygen they transport to economically synthesize adenosine triphosphate (ATP) as other normal differentiated cells do. Instead, red blood cells depend entirely on anaerobic glycolysis to cycle nicotinamide adenine dinucleotide (NAD$^+$) and to make ATP, an essential energy source largely used to drive ATPase-dependent K$^+$/Na$^+$ and Ca$^{2+}$ pumps, in order to maintain cell membrane integrity and pliability as they navigate through blood vessels. In PKD disorder, two major distinctive metabolic abnormalities are ATP depletion and concomitant increase of 2,3-diphosphoglycerate consistent with accumulation of upper glycolytic intermediates. Moreover, one of the consequences of decreased ATP and pyruvate level is lowered lactate level leading to inability to regenerate NAD$^+$ through lactate dehydrogenase for further use in glycolysis. The lack of ATP disturbs the cation gradient across the red cell membrane, causing the loss of potassium and water, which causes cell dehydration, contraction, and crenation, and leads to premature destruction and diminished lifetime of the red blood cells (RBCs). Such defective RBCs are destroyed in the spleen, and excessive hemolysis rate in the spleen leads to the manifestation of hemolytic anemia. The exact mechanism by which PKD sequesters newly matured RBCs in the spleen to effectively shorten overall half-lives of circulating RBCs is not yet clear, but recent studies suggest that metabolic dysregulation affects not only cell survival but also the maturation process resulting in ineffective erythropoiesis (Aizawa, S. et al., Exp Hematol 2005, 33 (11), 1292-8).

Pyruvate kinase catalyzes the transfer of a phosphoryl group from phosphoenolpyruvate (PEP) to ADP, yielding one molecule of pyruvate and one molecule of ATP. The enzyme has an absolute requirement for Mg$^{2+}$ and K$^+$ cations to drive catalysis. PK functions as the last critical step in glycolysis because it is an essentially irreversible reaction under physiological conditions. In addition to its role of synthesizing one of the two ATP molecules from the metabolism of glucose to pyruvate, pyruvate kinase is also an important cellular metabolism regulator. It controls the carbon flux in lower-glycolysis to provide key metabolite intermediates to feed biosynthetic processes, such as pentose-phosphate pathway among others, in maintaining healthy cellular metabolism. Because of these critical functions, pyruvate kinase is tightly controlled at both gene expression and enzymatic allostere levels. In mammals, fully activated pyruvate kinase exists as a tetrameric enzyme. Four different isozymes (M1, M2, L and R) are expressed from two separate genes. Erythrocyte-specific isozyme PKR is expressed from the PKLR gene ("L gene") located on chromosome 1q21. This same gene also encodes the PKL isozyme, which is predominately expressed in the liver. PKLR consists of 12 exons with exon 1 is erythroid-specific whereas exon 2 is liver-specific. The two other mammalian isozymes PKM1 and PKM2 are produced from the PKM gene ("M gene") by alternative splicing events controlled by hnRNP proteins. The PKM2 isozyme is expressed in fetal tissues and in adult proliferating cells such as cancer cells. Both PKR and PKM2 are in fact expressed in proerythroblasts. However, upon erythroid differentiation and maturation, PKM2 gradually is decreased in expression and progressively replaced by PKR in mature erythrocytes.

Clinically, hereditary PKR deficiency disorder manifests as non-spherocytic hemolytic anemia. The clinical severity of this disorder range from no observable symptoms in fully-compensated hemolysis to potentially fatal severe anemia requiring chronic transfusions and/or splenectomy at early development or during physiological stress or serious infections. Most affected individuals who are asymptomatic, paradoxically due to enhanced oxygen-transfer capacity, do not require any treatment. However, for some of the most severe cases, while extremely rare population-wise with estimated prevalence of 51 per million (Beutler, E. Blood 2000, 95 (11), 3585-8), there is no disease-modifying treatment available for these patients other than palliative care (Tavazzi, D. et al., Pediatr Ann 2008, 37 (5), 303-10). These hereditary non-spherocytic hemolytic anemia (HNSHA) patients present a clear unmet medical need.

Heterogenous genetic mutations in PKR lead to dysregulation of its catalytic activity. Since the initial cloning of PKR and report of a single point mutation Thr$^{384}$>Met associated with a HNSHA patient (Kanno, H. et al., Proc Natl Acad Sci USA 1991, 88 (18), 8218-21), there are now nearly 200 different reported mutations associated with this disease reported worldwide (Zanella, A. et al., Br J Haematol 2005, 130 (1), 11-25; Kedar, P., et al., Clin Genet 2009, 75 (2), 157-62; Fermo, E. et al., Br J Haematol 2005, 129 (6), 839-46; Pissard, S. et al., Br J Haematol 2006, 133 (6), 683-9). Although these mutations represent wide range genetic lesions that include deletional and transcriptional or translational abnormalities, by far the most common type is missense mutation in the coding region that one way or another affects conserved residues within domains that are structurally important for optimal catalytic function of PKR. The pattern of mutation prevalence seems to be unevenly distributed toward specific ethnic backgrounds. For instance, the most frequent codon substitutions reported for North American and European patients appear to be Arg$^{486}$>Trp and Arg$^{510}$>Gln, while mutations Arg$^{479}$>His, Arg$^{490}$>Trp and Asp$^{331}$>Gly were more frequently found in Asian patients (Kedar, P., et al., Clin Genet 2009, 75 (2), 157-62).

The present invention provides a method for increasing lifetime of the red blood cells (RBCs) in need thereof comprising contacting blood with an effective amount of (1) a compound of formula (I) or (II) or a pharmaceutically acceptable salt thereof; (2) a composition comprising a compound of formula (I) or (II) or a salt thereof and a carrier; or (3) a pharmaceutical composition comprising a compound of formula (I) or (II) or a pharmaceutically acceptable salt thereof and a pharmaceutically acceptable carrier:

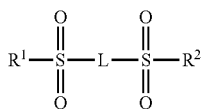
formula (I)

wherein $R^1$ and $R^2$ are aryl or heteroaryl, optionally substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alkylenedioxy, $OR^4$, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen; and L is a linker comprising an amino group; or a pharmaceutically acceptable salt thereof; with the provisos that W and $R^2$ are not dimethoxyphenyl or W and $R^2$ are not both 4-methylphenyl simultaneously

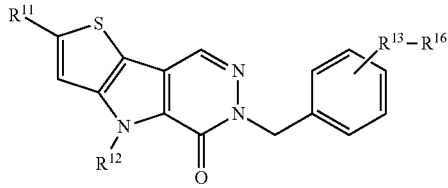
formula (II)

wherein:
$R^{11}$ is selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, $OR^{17}$, $SR^{17}$, $SOR^{17}$, $SO_2R^{17}$, $NR^{17}R^{18}$, $NCOR^{17}$, $SCOR^{17}$, $COR^{17}$, $OCOR^{17}$, $B(OH)_2$, $NO_2$, $NHCOR^{17}$, CN, CHO, hydroxyl $C_1$-$C_{10}$ alkyl, and halogen, $R^{12}$ is selected from the group consisting of H, $C_1$-$C_2$ alkyl, $C_3$-$C_{10}$ cycloalkyl, $NCOR^{14}$, and $SO_2R^{14}$, $R^{13}$ to $R^{16}$ are selected from the group consisting of H, $C_1$-$C_{10}$ alkyl, halo $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, heteroaryl, $OR^{17}$, $SR^{17}$, $NR^{17}R^{18}$, $NCOR^{17}$, $OCOR^{17}$, $SCOR^{17}$, $SOR^{17}$, $SO_2R^{17}$, $SO_2NR^{17}R^{18}$, $CF_3$, and halogen, and $R^{17}$ and $R^{18}$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, and $C_6$-$C_{10}$ aryl.

The present invention further provides a method for regulating 2,3-diphosphoglycerate levels in blood in need thereof comprising contacting blood with an effective amount of (1) a compound of formula (I) or (II) or a pharmaceutically acceptable salt thereof; (2) a composition comprising a compound of formula (I) or (II) or a salt thereof and a carrier; or (3) a pharmaceutical composition comprising a compound of formula (I) or (II) or a pharmaceutically acceptable salt thereof and a pharmaceutically acceptable carrier.

The present invention also provides a method for treating hereditary non-spherocytic hemolytic anemia comprising administering to a patient in need thereof a therapeutically effective amount of (1) a compound of formula (I) or (II) or a pharmaceutically acceptable salt thereof; (2) a pharmaceutical composition comprising a compound of formula (I) or (II) or a pharmaceutically acceptable salt thereof and a pharmaceutically acceptable carrier.

The present invention further provides a method for treating sickle cell anemia comprising administering to a patient in need thereof a therapeutically effective amount of (1) a compound of formula (I) or (II) or a pharmaceutically acceptable salt thereof; (2) a pharmaceutical composition comprising a compound of formula (I) or (II) or a pharmaceutically acceptable salt thereof and a pharmaceutically acceptable carrier.

The present invention further provides a method for treating hemolytic anemia (e.g., chronic hemolytic anemia caused by phosphoglycerate kinase deficiency, Blood Cells Mol Dis, 2011; 46(3):206) comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present invention further provides a method for treating thalassemia (e.g. beta-thalassemia), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), or anemia of chronic diseases comprising administering to a patient in need thereof a therapeutically effective amount of (1) a compound of formula (I) or (II) or a pharmaceutically acceptable salt thereof; (2) a pharmaceutical composition comprising a compound of formula (I) or (II) or a pharmaceutically acceptable salt thereof and a pharmaceutically acceptable carrier.

The present invention further provides a method for treating diseases or conditions that are associated with increased 2,3-diphosphoglycerate levels (e.g., liver diseases (Am J Gastroenterol, 1987; 82(12):1283) and Parkinson's (J. Neurol, Neurosurg, and Psychiatry 1976, 39:952) comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

In an embodiment, the methods of the present invention comprise a compound of Formula I:

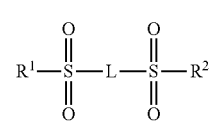
(I)

wherein $R^1$ and $R^2$ are aryl or heteroaryl, optionally substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alkylenedioxy, $OR^4$, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen, and L is a linker comprising an amino group;

or a pharmaceutically acceptable salt thereof;

with the provisos that $R^1$ and $R^2$ are not dimethoxyphenyl or $R^1$ and $R^2$ are not both 4-methylphenyl simultaneously.

In accordance with an embodiment, L is a linear amino group, cyclic amino group, or a combination thereof.

In another embodiment, the compound of formula I is a compound of formula (Ia):

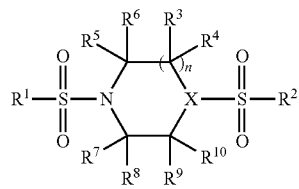

wherein n=1 to 3, $R^1$ and $R^2$ are aryl or heteroaryl optionally substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alkylenedioxy, $OR^4$, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen, $R^3$ and $R^4$ are independently selected from the group consisting of H, $C_1$-$C_{10}$, alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $COR^6$, F, and $CF_3$, or, $R^3$ and $R^4$, taken together, form C=O, $R^5$ and $R^7$ to $R^{10}$ are independently H, $C_1$-$C_{10}$ alkyl, or F, $R^6$ is $C_1$-$C_{10}$ alkyl or $C_3$-$C_{10}$ cycloalkyl, or each of $R^7$ and $R^8$ and of $R^9$ and $R^{10}$, together form C=O and X is CH or N, or a pharmaceutically acceptable salt thereof.

In an embodiment, the compound or salt according to the above described embodiments is a compound wherein $R^1$ and $R^2$ are phenyl substituted with one or more substituents selected from the group consisting of $C_1$-$C_{10}$ alkyl, $C_1$-$C_{10}$ trihaloalkyl, heterocyclyl, heteroaryl, alkylenedioxy, $OR^4$, $SR^4$, $NR^4R^5$, $NCOR^4$, $OCOR^4$, $SCOR^4$, $SOR^4$, $SO_2R^4$, $SO_2NR^4R^5$, CN, and halogen, $R^3$ and $R^4$ are independently selected from the group consisting of H, $C_1$-$C_{10}$ alkyl, and F, or, taken together, form C=O, and $R^5$ and $R^7$ to $R^{10}$ are independently H, $C_1$-$C_{10}$ alkyl, or F.

In any of the embodiments above, $R^1$ and $R^2$ are phenyl substituted with one or more substituents selected from the group consisting of $C_1$-$C_{10}$ alkyl, $C_1$-$C_{10}$ trihaloalkyl, heterocyclyl, heteroaryl, alkylenedioxy, CN, and halogen, and $R^3$ to $R^{10}$ are H.

In an embodiment of the compounds described above, X is N.

In an embodiment of the compounds described above, n is 1.

Some examples of the compounds described above include those wherein $R^1$ is selected from the group consisting of phenyl, 4-methylphenyl, 2-methylphenyl, 2-fluorophenyl, 4-chlorophenyl, 4-fluorophenyl, 4,2-difluorophenyl, 2,6-difluorophenyl, 2,4,5-trifluorophenyl, 4 chloro-2-fluorophenyl, 3-chloro-2-fluorophenyl, 4-trifluoromethylphenyl, 3 trifluoromethylphenyl, 2,6-difluoro-4-trifluoromethylphenyl, 2,6-difluoro-4-methoxyphenyl, 2,5 difluoro-4-propylphenyl, 2,6-difluoro-3-hydroxyphenyl, 2,4-difluorophenyl, 4-bromo-2 fluorophenyl, 2,6-difluoro-3-hydroxyphenyl, 3-methoxyphenyl, 4-methoxyphenyl, 4-cyanophenyl, 2-nitrophenyl, 2-pyridyl, 2-pyridyl-1-oxide, 2-(boronic acid)phenyl, 3-(boronic acid)phenyl, and 4-(boronic acid)phenyl; in some examples, $R^1$ is selected from the group consisting of 2,6-difluoro-4-trifluoromethylphenyl, 2,6-difluorophenyl, 2,6-difluoro-4-methoxyphenyl, 2,6-difluoro-3-hydroxyphenyl, and 4-methoxyphenyl.

In an embodiment, some examples of the compound of formula I-a is wherein $R^1$ is heterocyclyl or heteroaryl, selected from the group consisting of 2-pyridyl, 2-pyridyl-N-oxide, 3-pyridyl, 3-pyridyl-N-oxide, 4-pyridyl, 4-pyridyl-N-oxide, 2pyrimidinyl, 2-pyrimidinyl-N-oxide, 4-pyrimidinyl, 4-pyrimidinyl-N-oxide, 5-pyrimidinyl, 5pyrimidinyl-N oxide, 2-pyrazinyl, and 2-pyrazinyl-N-oxide.

In any of the embodiments above, $R^2$ is 6-(2,3-dihydrobenzo[b][1,4]dioxinyl), 7-(3,4-dihydro-2H-benzo[b][1,4]dioxepiinyl), 5-benzo[d][1,4]dioxinyl, 7-(4-methyl-3,4-dihydro-2H-pyrido[3,2-b][1,4-oxazinyl), 2-naphthalenyl, 6-(2,2-dimethylchromanyl), 5-(1-methyl-1H-indolyl), 6-(2-methylbenzo[d]thiazolyl), or 4-methoxyphenyl; in some embodiments, $R^2$ is 6-(2,3-dihydrobenzo[b][1,4]dioxinyl).

In keeping with the embodiments described above, specific examples of compounds include compounds of formula (Ia), wherein X is N, n=1, and $R^3$ to $R^{10}$ is H, and $R^1$ and $R^2$ are as follows:

$R^1$ is 4-methoxyphenyl and $R^2$ is 6-(2,3-dihydro-benzo[b][1,4]dioxinyl);

$R^1$ and $R^2$ are 6-(2,3-dihydro-benzo[b][1,4]dioxinyl);

$R^1$ and $R^2$ are 4-methoxyphenyl;

$R^1$ is 4-cyanophenyl and $R^2$ is 6-(2,3-dihydro-benzo[b][1,4]dioxinyl);

$R^1$ is 4-chlorophenyl and $R^2$ is 6-(2,3-dihydro-benzo[b][1,4]dioxinyl);

$R^1$ is 4-fluorophenyl and $R^2$ is 6-(2,3-dihydro-benzo[b][1,4]dioxinyl);

$R^1$ is 3-fluorophenyl and $R^2$ is 6-(2,3-dihydro-benzo[b][1,4]dioxinyl);

$R^1$ is 2-fluorophenyl and $R^2$ is 6-(2,3-dihydro-benzo[b][1,4]dioxinyl);

$R^1$ is 2,6-difluorophenyl and $R^2$ is 6-(2,3-dihydro-benzo[b][1,4]dioxinyl);

$R^1$ is 2,4,5-trifluorophenyl and $R^2$ is 6-(2,3-dihydro-benzo[b][1,4]dioxinyl);

$R^1$ is 2,6-difluoro-4-methoxyphenyl and $R^2$ is 6-(2,3-dihydro-benzo[b][1,4]dioxinyl);

$R^1$ is 2,5-difluoro-3-propylphenyl and $R^2$ is 6-(2,3-dihydro-benzo[b][1,4]dioxinyl);

$R^1$ is 2,6-difluoro-3-hydroxypheny and $R^2$ is 6-(2,3-dihydro-benzo[b][1,4]dioxinyl);

$R^1$ is 2,4-difluorophenyl and $R^2$ is 6-(2,3-dihydro-benzo[b][1,4]dioxinyl);

$R^1$ is phenyl and $R^2$ is 6-(2,3-dihydro-benzo[b][1,4]dioxinyl);

$R^1$ is 3-(trifluoromethylphenyl) and $R^2$ is 6-(2,3-dihydro-benzo[b][1,4]dioxinyl);

$R^1$ is 3-methoxyphenyl and $R^2$ is 6-(2,3-dihydro-benzo[b][1,4]dioxinyl);

$R^1$ is 4-methoxyphenyl and $R^2$ is 6-(2,3-dihydro-benzo[b][1,4]dioxinyl);

$R^1$ is 2-pyridyl and $R^2$ is 6-(2,3-dihydro-benzo[b][1,4]dioxinyl);

$R^1$ is 2-pyridyl-1-oxide and $R^2$ is 6-(2,3-dihydro-benzo[b][1,4]dioxinyl);

$R^1$ is 2,6-difluorophenyl and $R^2$ is 2,6-difluorophenyl;

$R^1$ is 2,6-difluorophenyl and $R^2$ is 7-(3,4-dihydro-2H-benzo[b][1,4]dioxepinyl);

$R^1$ is 2,6-difluorophenyl and $R^2$ is 5-benzo[d][1,4]dioxinyl;

$R^1$ is 2,6-difluorophenyl and $R^2$ is 7-(4-methyl-3,4-dihydro-2H-pyrido[3,2 b][1,4]oxazinyl);

$R^1$ is 2,6-difluorophenyl and $R^2$ is 2-naphthalenyl;

$R^1$ is 2,6-difluorophenyl and $R^2$ is 6-(2,2-dimethylchromanyl);

$R^1$ is 2,6-difluorophenyl and $R^2$ is 5-(1-methyl-1H-indolyl);

$R^1$ is 2,6-difluorophenyl and $R^2$ is 6-(2-methylbenzo[d]thiazolyl); or $R^1$ is 2,6-difluorophenyl and $R^2$ is 6-(2,3-dihydrobenzo[b][1,4]dioxinyl).

In accordance with another embodiment of the compound of formula Ia, X is CH. In an embodiment, n is 1. In any of these embodiments, $R^3$, $R^4$, and $R^5$ are H. Examples of such compounds include those wherein $R^1$ is selected from the group consisting of 4-methylphenyl, 2-methylphenyl, 2-fluorophenyl, 3-fluorophenyl, 2,4-difluorophenyl, 2,6-difluorophenyl, 2,4,5-trifluorophenyl, 2,6-difluoro-4-trifluoromethylphenyl, 4-chloro-2-fluoro, 3-chloro-2-fluoro, 4-trifluoromethylphenyl, 4bromo-2-fluorophenyl, 4-methoxyphenyl, and 2-nitrophenyl, particularly wherein $R^1$ is selected from the group consisting of 2,6-difluoro-4-trifluoromethylphenyl, 2,6-difluorophenyl, and 4-methoxyphenyl. In an embodiment of these compounds, $R^2$ is 3,4-ethylenedioxyphenyl.

In another embodiment of the compound of formula Ia is the compound of formula (Ib):

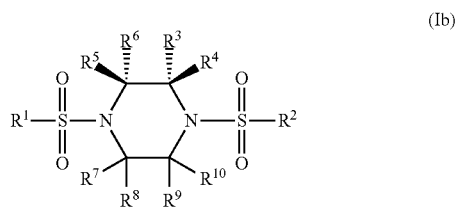
(Ib)

In a further embodiment, the compound is of formula (Ic):

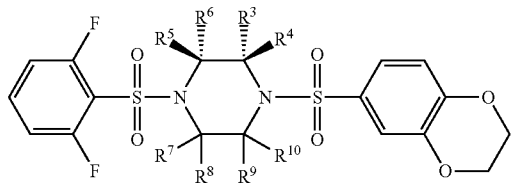
(Ic)

wherein $R^3$ to $R^{10}$ are H or methyl, $R^3$ to $R^6$ and $R^9$ and $R^{10}$ are H or methyl and $R^7$ form C=O, or $R^3$ to $R^8$ are H or methyl and $R^9$ and $R^{10}$ form C=O.

In accordance with an embodiment of the compound of formula (Ic), (i) $R^5$ is methyl and $R^3$, $R^4$, and $R^6$ to $R^{10}$ are H; (ii) $R^6$ is methyl and $R^3$ to $R^5$ and $R^7$ to $R^{10}$ are H; (iii) $R^3$ is methyl and $R^4$ to $R^{10}$ are H; (iv) $R^4$ is methyl and $R^3$ and $R^5$ to $R^{10}$ are H; (v) $R^3$ to $R^8$ are H and $R^9$ and $R^{10}$ form C=O; or (vi) $R^3$ to $R^6$ and $R^7$ and $R^8$ are H and $R^7$ and $R^8$ form C=O.

In accordance with an embodiment of the compound of formula I, L is an alkylene diamino group, cycloalkylamino amino, or cycloalkylamino alkylamino. Examples of compounds of this embodiment include compounds wherein L is N,N'-(ethane-1,2-diyl), N,N'-(propane-1,3-diyl), N,N'-(butane-1,4-diyl), N,N'-(pentane-1,5-diyl), N,N'-(hexane-1,6-diyl), N,N'-((trans)-cyclohexane-1,4-diyl), N,N'-((cis)-cyclohexane-1,4-diyl),

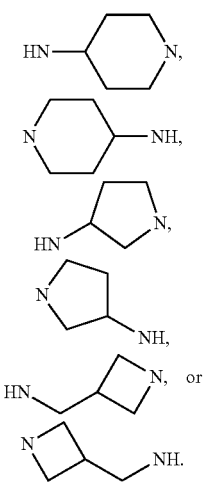

In an embodiment of the above compounds, $R^1$ is 2,6-difluorophenyl and $R^2$ is 6-(2,3-dihydrobenzo[b][1,4]dioxinyl).

In accordance with another embodiment, the invention provides a compound of Formula II:

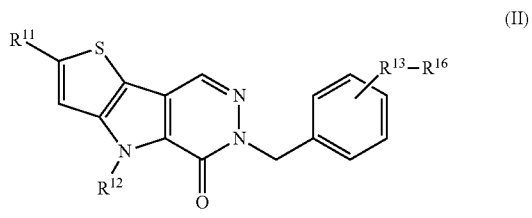
(II)

wherein:

$R^{11}$ is selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, $OR^{17}$, $SR^{17}$, $SOR^{17}$, $SO_2R^{17}$, $NR^{17}R^{18}$, $NCOR^{17}$, $SCOR^{17}$, $COR^{17}$, $OCOR^{17}$, $B(OH)_2$, $NO_2$, $NHCOR^{17}$, CN, CHO, hydroxyl $C_1$-$C_{10}$ alkyl, and halogen, $R^{12}$ is selected from the group consisting of H, $C_1$-$C_2$ alkyl, $C_3$-$C_{10}$ cycloalkyl, $NCOR^{14}$, and $SO_2R^{14}$, $R^{13}$ to $R^{16}$ are selected from the group consisting of H, $C_1$-$C_{10}$ alkyl, halo $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, heteroaryl, $OR^{17}$, $SR^{17}$, $NR^{17}R^{18}$, $NCOR^{17}$, $OCOR^{17}$, $SCOR^{17}$, $SOR^{17}$, $SO_2R^{17}$, $SO_2NR^{17}R^{18}$, $CF_3$, and halogen, and $R^{17}$ and $R^{18}$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, and $C_6$-$C_{10}$ aryl, or a pharmaceutically acceptable salt thereof, with the proviso that when $R^{11}$ is methyl, $R^{12}$ is methyl or allyl, and $R^{14}$ to $R^{16}$ are H, then $R^{13}$ is not methoxy or fluoro.

In accordance with an embodiment of the compound of formula II, $R^{11}$ is selected from the group consisting of H, $C_1$-$C_{10}$ alkyl, $OR^{17}$, $SR^{17}$, $SOR^{17}$, $SO_2R^{17}$, $NR^{17}R^{18}$, $NCOR^{17}$, $SCOR^{17}$, $COR^{17}$, $OCOR^{17}$, $B(OH)_2$, $NO_2$, $NHCOR^{17}$, CN, CHO, hydroxy $C_1$-$C_{10}$ alkyl, and halogen, $R^{12}$ is selected from the group consisting of H, methyl, $NCOR^{14}$, and $SO2R^{14}$, $R^{13}$ to $R^{16}$ are selected from the group consisting of H, $C_1$-$C_{10}$ alkyl, $OR^{17}$, $SR^{17}$, $NR^{17}R^{18}$, $NCOR^{17}$, $OCOR^{17}$, $SCOR^{17}$, $SOR^{17}$, $SO_2R^{17}$, $SO_2NR^{17}R^{18}$, $CF_3$, and halogen, and $R^{17}$ and $R^{18}$ are independently selected from the group consisting of H and $C_1$-$C_{10}$ alkyl.

In an embodiment of the compound of formula II, wherein $R^{11}$ is selected from the group consisting of H, $C_1$-$C_{10}$ alkyl, $OR^{17}$, $SR^{17}$, $SOR^{17}$, $COR^{17}$, $OCOR^{17}$, $B(OH)_2$, $NO_2$, $NHCOR^{17}$, CN, CHO, hydroxy $C_1$-$C_{10}$ alkyl, and halogen, $R^{12}$ is H or $C_1$-$C_2$ alkyl, and $R^{13}$ to $R^{16}$ are selected from the group consisting of H, methyl, $CF_3$, methoxy, and halogen.

Compounds described herein are activators of PKR mutants having lower activities compared to the wild type, thus are useful for methods of the present invention. Such mutations in PKR can affect enzyme activity (catalytic efficiency), regulatory properties (modulation by fructose bisphosphate (FBP)/ATP), and/or thermostability of the enzyme. Examples of such mutations are described in Valentini et al, JBC 2002. Some examples of the mutants that are activated by the compounds described herein include G332S, G364D, T384M, G37E, R479H, R479K, R486W, R532W, R510Q, and R490W. Without being bound by theory, compounds described herein affect the activities of PKR mutants by activating FBP non-responsive PKR mutants, restoring thermostability to mutants with decreased stability, or restoring catalytic efficiency to impaired mutants. The activating activity of the present compounds against PKR mutants may be tested following a method described in Example 1. Compounds described herein are also activators of wild type PKR.

In an embodiment, to increase the lifetime of the red blood cells, a compound, composition or pharmaceutical composition described herein is added directly to whole blood or packed cells extracorporeally or be provided to the patient directly (e.g., by i.p., i.v., i.m., oral, inhalation (aerosolized delivery), transdermal, sublingual and other delivery routes). Without being bound by theory, compounds described herein increase the lifetime of the RBCs, thus counteract aging of stored blood, by impacting the rate of release of 2,3-DPG from the blood. A decrease in the level of 2,3-DPG concentration induces a leftward shift of the oxygen-hemoglobin dissociation curve and shifts the allosteric equilibrium to the R, or oxygenated state, thus producing a therapeutic inhibition of the intracellular polymerization that underlies sickling by increasing oxygen affinity due to the 2,3-DPG depletion, thereby stabilizing the more soluble oxy-hemoglobin. Accordingly, in one embodiment, compounds and pharmaceutical compositions described herein are useful as antisickling agents. In another embodiment, to regulate 2,3-diphosphoglycerate, a compound, composition or pharmaceutical composition described herein is added directly to whole blood or packed cells extracorporeally or be provided to the patient directly (e.g., by i.p., i.v., i.m., oral, inhalation (aerosolized delivery), transdermal, sublingual and other delivery routes).

Referring now to terminology used generically herein, for compounds of formula I or II, the term "alkyl" means a straight-chain or branched alkyl substituent containing from, for example, 1 to about 6 carbon atoms, preferably from 1 to about 4 carbon atoms, more preferably from 1 to 2 carbon atoms. Examples of such substituents include methyl, ethyl, propyl, isopropyl, n-butyl, sec-butyl, isobutyl, tert-butyl, pentyl, isoamyl, hexyl, and the like.

The term "alkylene," as used herein, means a cyclic alkylene group fused to the phenyl group to which it is attached and containing from, for example about 3 to about 5 carbon atoms, preferably from about 3 to about carbon atoms. Examples of such substituents include, together with the phenyl, dihydroindenyl and 1,2,3,4-tetrahydronaphthyl.

The term "alkenyl," as used herein, means a linear alkenyl substituent containing at least one carbon-carbon double bond and from, for example, about 2 to about 6 carbon atoms (branched alkenyls are about 3 to about 6 carbons atoms), preferably from about 2 to about 5 carbon atoms (branched alkenyls are preferably from about 3 to about 5 carbon atoms), more preferably from about 3 to about 4 carbon atoms. Examples of such substituents include propenyl, isopropenyl, n-butenyl, sec-butenyl, isobutenyl, tert-butenyl, pentenyl, isopentenyl, hexenyl, and the like.

The term "alkynyl," as used herein, means a linear alkynyl substituent containing at least one carbon-carbon triple bond and from, for example, 2 to about 6 carbon atoms (branched alkynyls are about 3 to about 6 carbons atoms), preferably from 2 to about 5 carbon atoms (branched alkynyls are preferably from about 3 to about 5 carbon atoms), more preferably from about 3 to about 4 carbon atoms. Examples of such substituents include propynyl, isopropynyl, n-butynyl, sec-butynyl, isobutynyl, tert-butynyl, pentynyl, isopentynyl, hexynyl, and the like.

The term "cycloalkyl," as used herein, means a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The term "cycloalkenyl," as used herein, means the same as the term "cycloalkyl," however one or more double bonds are present. Examples of such substituents include cyclopentenyl and cyclohexenyl. The cyclic alkyl groups may be unsubstituted or further substituted with alkyl groups such as methyl groups, ethyl groups, and the like.

The term "heteroaryl," as used herein, refers to a monocyclic or bicyclic 5- or 6-membered aromatic ring system containing one or more heteroatoms selected from the group consisting of O, N, S, and combinations thereof. Examples of suitable monocyclic heteroaryl groups include but are not limited to furanyl, thiopheneyl, pyrrolyl, pyrazolyl, imidazolyl, 1,2,3-triazolyl, 1,2,4-triazolyl, isoxazolyl, oxazolyl, isothiazolyl, thiazolyl, pyridinyl, pyrimidinyl, pyrazinyl, and triazinyl. The heteroaryl group can be attached to the sulfonamide group at any available position on the heteroaryl group. For example, a thiopheneyl group can be attached at the 2-position or the 3-position of the thiopheneyl group. A pyridyl group can be attached at the 2-, 3-, or 4-position of the pyridyl group. Suitable bicyclic heterocycloaryl groups include monocylic heterocycloaryl rings fused to a $C_6$-$C_{10}$ aryl ring. Non-limiting examples of bicyclic heterocycloaryl groups include benzofuran, benzothiophene, quinoline, and isoquinoline. The heteroaryl group is optionally substituted with 1, 2, 3, 4, or 5 substituents as recited herein, wherein the optional substituent can be present at any open position on the heteroaryl group. The term "heteroaryl oxide," as used herein, refers to an oxidized heteroaryl group as that term is defined herein, wherein one or more of the heteroatoms comprising the heteroaryl group is oxidized. Non-limiting examples of heteroaryl oxide groups include pyridine N-oxide, pyrimidine N-oxide, and pyrazine N-oxide.

The term "heterocyclyl" refers to a cyclic group, which may be aromatic or nonaromatic, or saturated or unsaturated, having one or more heteroatoms such as O, N, or S. Examples of heterocyclyl groups include pyridyl, piperidinyl, piperazinyl, pyrazinyl, pyrolyl, pyranyl, tetrahydropyranyl, tetrahydrothiopyranyl, pyrrolidinyl, furanyl, tetrahydrofuranyl, thiophenyl, tetrahydrothiophenyl, purinyl, pyrimidinyl, thiazolyl, thiazolidinyl, thiazolinyl, oxazolyl, triazolyl, tetrazolyl, tetrazinyl, benzoxazolyl, morpholinyl, thiophorpholinyl, quinolinyl, and isoquinolinyl.

The term "halo" or "halogen," as used herein, means a substituent selected from Group VIIA, such as, for example, fluorine, bromine, chlorine, and iodine.

The term "aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise 4n+2π electrons, according to Huckel's Rule.

In an embodiment of the compound of formula II, $R^{11}$ is selected from the group consisting of H, methyl, ethyl, isopropyl, $OCH_3$, $SCH_3$, $S(O)CH_3$, $NO_2$, $NHCOCH_3$, $CN$, $COOCH_3$, $CHO$, $CH_2OH$, $B(OH)_2$, and $CH(OH)CH_3$, $R^{12}$ is methyl, $R^{13}$ is 2-fluoro or chloro, and $R^{14}$ to $R^{16}$ are H.

In any of the embodiments of the compound of formula II, $R^{11}$ and $R^{12}$ are methyl, $R^{13}$ is H, 2-fluoro, 3-fluoro, 4-fluoro, 2-chloro, 3-chloro, 4-chloro, 4-$CF_3$, 4-methyl, or 4-methoxy, and $R^{14}$ to $R^{16}$ are H. Examples of $R^{11}$ and $R^{12}$ are methyl, and of $R^{13}$ and $R^{14}$ are 2-fluoro and 4-fluoro, 2-fluoro and 6-fluoro, 2-fluoro and 3-fluoro, 2-choro and 6-fluoro, 2-fluoro and 3-methyl, 2-fluoro and 4-methyl, 2-fluoro and 4-$CF_3$, and 2-fluoro and 4-methoxy, and of $R^{15}$ and $R^{16}$ are H.

In an embodiment of the compound of the formula II, $R^{11}$ and $R^{12}$ are methyl, $R^{13}$ to $R^{15}$ are 2-fluoro, 3-fluoro, and 4-fluoro, and $R^{16}$ is H. In another specific embodiment of the compound of formula II, $R^{11}$ and $R^{12}$ are methyl, $R^{13}$ to $R^{16}$ are 2-fluoro, 3-fluoro, 5-fluoro, and 6-fluoro.

The invention provides the use of a compound or a pharmaceutically acceptable salt thereof in the manufacture of a medicament for increasing lifetime of the red blood cells (RBCs) in a patient in need thereof (e.g., the medicament is provided to the patient directly, e.g., i.p., i.v., i.m., oral, inhalation (aerosolized delivery), transdermal, sublingual and other delivery routes), wherein the compound is of formula I, Ia, Ib, Ic, Id, II, IIa or III.

The invention further provides the use of a compound or a pharmaceutically acceptable salt thereof in the manufacture of a medicament for regulating 2,3-diphosphoglycerate levels in blood in a patient in need thereof (e.g., the medicament is provided to the patient directly, e.g., by i.p., i.v., i.m., oral, inhalation (aerosolized delivery), transdermal, sublingual and other delivery routes), wherein the compound is of formula I, Ia, Ib, Ic, Id, II, IIa or III.

The invention also provides the use of a compound or a pharmaceutically acceptable salt thereof in the manufacture of a medicament for treating hereditary non-spherocytic hemolytic anemia in a patient in need thereof, wherein the compound is of formula I, Ia, Ib, Ic, Id, II, IIa or III.

The invention further provides the use of a compound or a pharmaceutically acceptable salt thereof in the manufacture of a medicament for treating sickle cell anemia comprising administering to a patient in need thereof, wherein the compound is of formula I, Ia, Ib, Ic, Id, II, IIa or III.

The invention further provides the use of a compound or a pharmaceutically acceptable salt thereof in the manufacture of a medicament for treating thalassemia, hereditary spherocytosis, hereditary elliptocytosis, abetalipoproteinemia (or Bassen-Kornzweig syndrome), paroxysmal nocturnal hemoglobinuria, or acquired hemolytic anemia comprising administering to a patient in need thereof, wherein the compound is of formula I, Ia, Ib, Ic, Id, II, IIa or III.

In accordance with a further embodiment, a compound of the invention is represented by Formula Id:

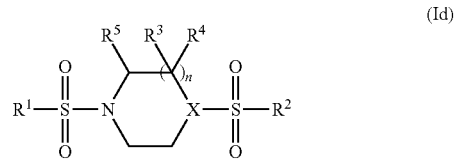

wherein n=1 to 3, $R^1$ and $R^2$ are phenyl substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heteroaryl, heteroaryloxide, alkylenedioxy, $OR^4$, $SR^4$, $NR^4R^5$, $NCOR^4$, $OCOR^4$, $SCOR^4$, $SOR^4$, $SO_2R^4$, $SO_2NR^4R^5$, nitro, boronic acid, and halogen, $R^3$ and $R^4$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $COR^6$, F, and $CF_3$, or, taken together, form C=O, $R^5$ is H, $C_1$-$C_{10}$ alkyl, or P, $R^6$ is $C_1$-$C_{10}$ alkyl or $C_3$-$C_{10}$ cycloalkyl, and X is CH or N, or a pharmaceutically acceptable salt thereof, with the provisos that (1) when X is N, n=1, and $R^3$, $R^4$, and $R^5$ are H or when X is N, n=1, and one of $R^3$, $R^4$, and $R^5$ is alkyl, $R^1$ is not dimethoxyphenyl and (2) that $R^1$ and $R^2$ are not both 4-methylphenyl.

In certain embodiments of formula (Id), $R^1$ and $R^2$ are phenyl substituted with one or more substituents selected from the group consisting of $C_1$-$C_{10}$ alkyl, $C_1$-$C_{10}$ trihaloalkyl, alkylenedioxy, $OR^4$, $SR^4$, $NR^4R^5$, $NCOR^4$, $OCOR^4$, $SCOR^4$, $SOR^4$, $SO_2R^4$, $SO_2NR^4R^5$, and halogen, wherein $R^3$ and $R^4$ are independently selected from the group consisting of H, $C_1$-$C_{10}$ alkyl, and F, or, taken together, form C=O, and $R^5$ is H, $C_1$-$C_{10}$ alkyl, or F.

In any of the embodiments of formula (Id), $R^1$ and $R^2$ are phenyl substituted with one or more substituents selected from the group consisting of $C_1$-$C_{10}$ alkyl, $C_1$-$C_{10}$ trihaloalkyl, alkylenedioxy, and halogen, and $R^3$, $R^4$, and $R^5$ are H.

In certain embodiments of formula (Id), X is N and n is 1-3. In accordance with an embodiment, n is 1. In some embodiments, $R^1$ is selected from the group consisting of 4-methylphenyl, 2-methylphenyl, 2-fluorophenyl, 3-fluorophenyl, 4,2-difluorophenyl, 2,6-difluorophenyl, 2,4,5-trifluorophenyl, 4-chloro-2-fluorophenyl, 3-chloro2-fluorophenyl, 4-trifluoromethylphenyl, 2,6-difluoro-4-trifluoromethylphenyl, 4-bromo-2-fluorophenyl, 4-methoxyphenyl, 2-nitrophenyl, 2-(boronic acid)phenyl, 3-(boronic acid)phenyl, and 4-(boronic acid)phenyl. In other embodiments, $R^1$ is selected from the group consisting of 2,6 difluoro-4-trifluoromethylphenyl, 2,6-difluorophenyl, and 4-methoxyphenyl.

In some embodiments of formula (Id), $R^2$ is 3,4-ethylenedioxyphenyl.

In certain preferred embodiments of the compounds of formula (Id), the invention provides a compound selected from the group consisting of 1-(2,3-dihydrobenzo[b][1,4[dioxin-S-ylsulfonyl)-4-(4-methylphenylphenylsulfonyl)piperazine, 1-(2,3-dihydrobenzo[b][1,4[dioxin-S-ylsulfonyl)-4-(2-methylphenylsulfonyl)piperazine, 1-(2,3-dihydrobenzo[b][1,4]dioxin-6-ylsulfonyl)-4-(2-fluorophenylsulfonyl)piperazine, 1-(2,3-dihydrobenzo[b][1,4]dioxin-6-ylsulfonyl)-4-(3-fluorophenylsulfonyl)piperazine, 1-(2,3-dihydrobenzo[b][1,4]dioxin-6-ylsulfonyl)-4-(2,4-difluorophenylsulfonyl)piperazine, 1-(2,3-dihydrobenzo[b][1,4]dioxin-6-ylsulfonyl)-4-(2,6-difluorophenylsulfonyl)

piperazine, 1-(2,3-dihydrobenzo[b][1,4[dioxin-S-ylsulfonyl)-4-(2,4,5-trifluorophenylsulfonyl)piperazine, 1-(2,3-dihydrobenzo[b][1,4]dioxin-6-ylsulfonyl)-4-(4-chloro-2-fluorophenylsulfonyl)piperazine, 1(2,3-dihydrobenzo[b][1,4]dioxin-6-ylsulfonyl)-4-(3-chloro-2-fluorophenylsulfonyl) piperazine, 1-(2,3-dihydrobenzo[b][1,4]dioxin-6-ylsulfonyl)-4-(4-trifluoromethylphenylsulfonyl)piperazine, 1-(2,3-dihydrobenzo[b][1,4]dioxin-6-ylsulfonyl)-4-(2,6-difluoro-4-trifluoromethlphenylsulfonyl)piperazine, 1-(2,3-dihydrobenzo[b][1,4]dioxin-6-ylsulfonyl)-4-(4-bromo-2-fluorophenylsulfonyl)piperazine, 1(2,3-dihydrobenzo[b][1,4]dioxin-6-ylsulfonyl)-4-(4-methoxyphenylsulfonyl)piperazine, 1(2,3-dihydrobenzo[b][1,4]dioxin-6-ylsulfonyl)-4-(2-nitrophenylsulfonyl)piperazine, 1(2,3-dihydrobenzo[b][1,4]dioxin-6-ylsulfonyl)-4-(2-(boronic acid)phenylsulfonyl)piperazine, 1(2,3-dihydrobenzo[b][1,4]dioxin-S-ylsulfonyl)-4-(3-(boronic acid)phenylsulfonyl)piperazine, and 1-(2,3-dihydrobenzo[b][1,4]dioxin-6-ylsulfonyl)-4-(4-(boronic acid)phenylsulfonyl)piperazine.

It will be understood that the terms 2-(boronic acid)phenyl, 3-(boronic acid)phenyl, and 4-(boronic acid)phenyl refer to a group of the formula:

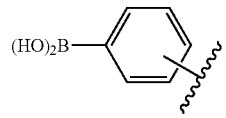

wherein the phenyl group is attached to the sulfonyl group at the 2-, 3-, or 4-position of the phenyl ring.

In certain embodiments of formula (Id), one of $R^3$, $R^4$, or $R^5$ is $C_1$-$C_{10}$ alkyl and two of $R^3$, $R^4$, and $R^5$ are H. In certain embodiments, a compound of the present invention is selected from the group consisting of 1-(2,6-difluorophenylsulfonyl)4(2,3-dihydrobenzo[b]dioxin-6-ylsulfonyl)-2-methylpiperazine or 1-(2,6-difluorophenylsulfonyl)-4-(2,3-dihydrobenzo[b]dioxin-6-ylsulfonyl)-3-methylpiperazine. It will be recognized that when one of $R^3$, $R^4$, or $R^5$ is $C_1$-$C_{10}$ alkyl, the carbon to which $R^3$, $R^4$, or $R^5$ is $C_1$-$C_{10}$ alkyl is attached is a chiral carbon center.

The invention contemplates embodiments in which a compound having a chiral center is a substantially pure enantiomer thereof, a racemic mixture thereof, or a mixture containing any proportion of the two enantiomers thereof.

In certain embodiments of formula (Id), one of $R^3$, $R^4$, or $R^5$ is F. In accordance with these embodiments, two of $R^3$, $R^4$, or $R^5$ are independently H or $C_1$-$C_{10}$ alkyl, or when $R^5$ is F, $R^3$ and $R^4$, taken together, can be C=O.

In certain embodiments of formula (Id), $R^3$ and $R^4$, taken together, can be C=O. In these embodiments, $R^5$ is H, F, or $C_1$-$C_{10}$ alkyl. In a specific embodiment, the invention provides a compound that is 1-(2,6-difluorophenylsulfonyl)-4-(2,3-dihydrobenzo[b]dioxin-6ylsulfonyl)-3-oxopiperazine.

In certain embodiments of formula (Id), $R^1$ is selected from the group consisting of 2-pyridyl, 2-pyridyl-N-oxide, 3-pyridyl, 3-pyridyl-N-oxide, 4-pyridyl, 4-pyridyl-N-oxide, 2-pyrimidinyl, 2-pyrimidinyl-N-oxide, 4-pyrimidinyl, 4-pyrimidinyl-N-oxide, 5-pyrimidinyl, 5-pyrimidinyl-N-oxide, 2-pyrazinyl, and 2-pyrazinyl-N-oxide. In some embodiments, $R^1$ is selected from the group consisting of 2-pyridyl, 3-pyridyl, and 4-pyridyl. In some embodiments, $R^1$ is selected from the group consisting of 2-pyridyl-N-oxide, 3pyridyl-N-oxide, and 4-pyridyl-N-oxide. In some embodiments, $R^2$ is 3,4-ethylenedioxyphenyl.

In certain embodiments of formula (Id), X is CH and n is 1-3. In accordance with some embodiments, n is 1. In these embodiments, $R^1$, $R^2$, $R^3$, $R^4$, and $R^5$ are as defined previously herein. In one embodiment, a compound of the present invention is 1-(2,6-difluorophenylsulfonyl)-4-(2,3-dihydrobenzo[b]dioxin-6-ylsulfonyl)-piperidine.

In accordance with another embodiment, a compound of the present invention is represented by Formula IIa:

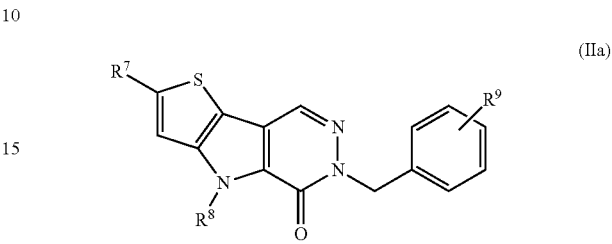

(IIa)

wherein:
$R^7$ is selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, $OR^{10}$, $SR^{10}$, $SOR^{10}$, $SO_2R^{10}$, $NR^{10}R^{11}$, $NCOR^{10}$, $SCOR^{10}$, $OCOR^{10}$, $B(OH)_2$, and halogen, $R^8$ is selected from the group consisting of $C_1$-$C_{10}$ alkyl, $C_3$-$C_{10}$ cycloalkyl, $NCOR^{10}$, and $SO_2R^{10}$, $R^9$ is selected from the group consisting of $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, heteroaryl, $OR^{10}$, $NR^{10}R^{11}$, $NCOR^{10}$, $OCOR^{10}$, $SCOR^{10}$, $SOR^{10}$, $SO_2R^{10}$, $SO_2NR^{10}R^{11}$, $CF_3$, and halogen, and $R^{10}$ and $R^{11}$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, and $C_6$-$C_{10}$ aryl, or a pharmaceutically acceptable salt thereof, with the proviso that when $R^7$ is methyl and $R^8$ is methyl or allyl, $R^9$ is not methoxy or fluoro.

In certain embodiments of formula (IIa), $R^7$ is selected from the group consisting of H, $C_1$-$C_{10}$ alkyl, $OR^{10}$, $SR^{10}$, $SOR^{10}$, $SO2R^{10}$, $NR^{10}R^{11}$, $NCOR^{10}$, $SCOR^{10}$, $OCOR^{10}$, $B(OH)_2$, and halogen, $R^8$ is selected from the group consisting of $C_1$-$C_{10}$ alkyl, $NCOR^{10}$, and $SO_2R^{10}$, $R^9$ is selected from the group consisting of $C_1$-$C_{10}$ alkyl, $OR^{10}$, $SR^{10}$, $NR^{10}R^{11}$, $NCOR^{10}$, $OCOR^{10}$, $SCOR^{10}$, $SOR^{10}$, $SO_2R^{10}$, $SO_2NR^{10}R^{11}$, $CF_3$, and halogen, and $R^{10}$ and $R^{11}$ are independently selected from the group consisting of H and $C_1$-$C_{10}$ alkyl. In some embodiments, $R^7$ is selected from the group consisting of H, $C_1$-$C_{10}$ alkyl, or halogen, $R^8$ is $C_1$-$C_{10}$ alkyl, and $R^9$ is selected from the group consisting of $C_1$-$C_{10}$ alkyl, $CF_3$, and halogen.

In certain embodiments of formula (IIa), $R^9$ is 2-fluoro. In accordance with these embodiments, $R^7$ is selected from the group consisting of H, Br, ethenyl, ethyl, propenyl, and propyl, and $R^8$ is methyl. In some embodiments, a compound of the present invention is selected from the group consisting of 4-methyl-4H-thieno[3,2-b]pyrrole-2-(2-fluoro benzyl)pyridazin-3(2H)one, 2-bromo-4-methyl-4H-thieno[3,2-b]pyrrole-2-(2-fluorobenzyl)pyridazin-3(2H)one, 4-methyl-2-vinyl-4H-thieno[3,2-b]pyrrole-2-(2-fluorobenzyl) pyridazin-3(2H)one, 2-ethyl-4-methyl-4H-thieno[3,2-b]pyrrole-2-(2-fluorobenzyl)pyridazin-3(2H)one, 4-methyl-(2-(prop-1-en2-yl)-4H-thieno[3,2-b]pyrrole-2(2-fluorobenzyl)pyridazin-3(2H)one, and 2-isopropyl-4-methyl-4H-thieno[3,2-b]pyrrole-2(2-fluorobenzyl)pyridazin-3(2H)one.

The present invention provides a method for increasing lifetime of the red blood cells (RBCs) in need thereof comprising contacting blood with an effective amount of (1) a compound of formula (III) or a pharmaceutically acceptable salt thereof; (2) a composition comprising a compound of formula (III) or a salt thereof and a carrier; or (3) a pharmaceutical composition comprising a compound of formula (III) or a pharmaceutically acceptable salt thereof and a pharmaceutically acceptable carrier:

wherein $R^{21}$ and $R^{22}$ are aryl, substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alkylenedioxy, $OR^{23}$, $SR^{23}$, $NR^{23}R^{24}$, $NCOR^{23}$, $OCOR^{23}$, $SCOR^{23}$, $SO_2R^{23}$, $SO_2NR^{23}R^{24}$, $NO_2$, $B(OH)_2$, CN and halogen, wherein $R^{23}$ and $R^{24}$ are independently H, $C_1$-$C_{10}$ alkyl, F, $C_2$-$C_{10}$ alkenyl, $C_2$-$C_{10}$ alkynyl, $C_3$-$C_{10}$ cycloalkyl, $C_3$-$C_{10}$ cycloalkenyl, $COR_6$, and $CF_3$, or a pharmaceutically acceptable salt thereof.

The present invention further provides a method for regulating 2,3-diphosphoglycerate levels in blood in need thereof comprising contacting blood with an effective amount of (1) a compound of formula (III) or a pharmaceutically acceptable salt thereof; (2) a composition comprising a compound of formula (III) or a salt thereof and a carrier; or (3) a pharmaceutical composition comprising a compound of formula (III) or a pharmaceutically acceptable salt thereof and a pharmaceutically acceptable carrier.

The present invention also provides a method for treating hereditary non-spherocytic hemolytic anemia comprising administering to a patient in need thereof a therapeutically effective amount of (1) a compound of formula (III) or a pharmaceutically acceptable salt thereof; (2) a pharmaceutical composition comprising a compound of formula (III) or a pharmaceutically acceptable salt thereof and a pharmaceutically acceptable carrier.

The present invention further provides a method for treating sickle cell anemia comprising administering to a patient in need thereof a therapeutically effective amount of (1) a compound of formula (III) or a pharmaceutically acceptable salt thereof; (2) a pharmaceutical composition comprising a compound of formula (III), or a pharmaceutically acceptable salt thereof and a pharmaceutically acceptable carrier.

The present invention further provides a method for treating thalassemia, hereditary spherocytosis, hereditary elliptocytosis, abetalipoproteinemia (or Bassen-Kornzweig syndrome), paroxysmal nocturnal hemoglobinuria, or acquired hemolytic anemia comprising administering to a patient in need thereof a therapeutically effective amount of (1) a compound of formula (III) or a pharmaceutically acceptable salt thereof; (2) a pharmaceutical composition comprising a compound of formula (III) or a pharmaceutically acceptable salt thereof and a pharmaceutically acceptable carrier.

In accordance with an embodiment of formula III, a compound of the present invention is the following compound or salt thereof:

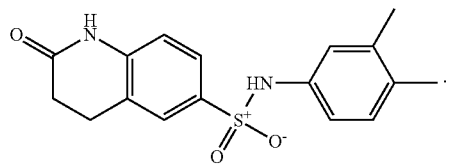 [SMILES: Cc1ccc(N[S+](=O)([O-])c2ccc3c(c2)CCC(=O)N3)cc1C]

The phrase "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media such as ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p. 1445, and *Journal of Pharmaceutical Science,* 66, 2-19 (1977).

Suitable bases include inorganic bases such as alkali and alkaline earth metal bases, e.g., those containing metallic cations such as sodium, potassium, magnesium, calcium and the like. Non-limiting examples of suitable bases include sodium hydroxide, potassium hydroxide, sodium carbonate, and potassium carbonate. Suitable acids include inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, maleic acid, tartaric acid, fatty acids, long chain fatty acids, and the like. Preferred pharmaceutically acceptable salts of inventive compounds having an acidic moiety include sodium and potassium salts. Preferred pharmaceutically acceptable salts of inventive compounds having a basic moiety (e.g., a pyridyl group) include hydrochloride and hydrobromide salts. The compounds of the present invention containing an acidic or basic moiety are useful in the form of the free base or acid or in the form of a pharmaceutically acceptable salt thereof.

It should be recognized that the particular counterion forming a part of any salt of this invention is usually not of a critical nature, so long as the salt as a whole is pharmacologically acceptable and as long as the counterion does not contribute undesired qualities to the salt as a whole.

It is further understood that the above compounds and salts may form solvates, or exist in a substantially uncomplexed form, such as the anhydrous form. As used herein, the term "solvate" refers to a molecular complex wherein the solvent molecule, such as the crystallizing solvent, is incorporated into the crystal lattice. When the solvent incorporated in the solvate is water, the molecular complex is called a hydrate. Pharmaceutically acceptable solvates include hydrates, alcoholates such as methanolates and ethanolates, acetonitrilates and the like. These compounds can also exist in polymorphic forms.

Carriers and pharmaceutically acceptable carriers of the present invention are those that is chemically inert to the active compounds and one that has no detrimental side effects or toxicity under the conditions of use.

The choice of carrier will be determined in part by the particular compound of the present invention chosen, as well as by the particular method used to apply/administer the composition. Accordingly, there are wide variety of suitable formulations of the pharmaceutical composition of the present invention. The following formulations for oral, aerosol, parenteral, subcutaneous, intravenous, intramuscular, intraperitoneal, intrathecal, rectal, and vaginal administration are merely exemplary and are in no way limiting.

The pharmaceutical composition can be administered parenterally, e.g., intravenously, subcutaneously, intradermally, or intramuscularly. Thus, the invention provides compositions for parenteral administration that comprise a solution of the inventive compound or salt dissolved or suspended in an acceptable carrier suitable for parenteral administration, including aqueous and non-aqueous isotonic sterile injection solutions.

Overall, the requirements for effective pharmaceutical carriers for parenteral compositions are well known to those of ordinary skill in the art. See, e.g., Banker and Chalmers, eds., *Pharmaceutics and Pharmacy Practice*, J. B. Lippincott Company, Philadelphia, pp. 238-250 (1982), and Toissel, *ASHP Handbook on Injectable Drugs*, 4th ed., pp. 622-630 (1986). Such solutions can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound or salt of the present invention may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-beta-aminopropionates, and 2-alkyl-imidazoline quaternary ammonium salts, and (e) mixtures thereof.

The parenteral formulations can contain preservatives and buffers. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Topical formulations, including those that are useful for transdennal drug release, are well-known to those of skill in the art and are suitable in the context of the invention for application to skin.

Formulations suitable for oral administration can consist of (a) liquid solutions, such as a therapeutically effective amount of the inventive compound dissolved in diluents, such as water, saline, or orange juice, (b) capsules, sachets, tablets, lozenges, and troches, each containing a predetermined amount of the active ingredient, as solids or granules, (c) powders, (d) suspensions in an appropriate liquid, and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compound or salt of the present invention, alone or in combination with other suitable components, can be made into aerosol formulations to be administered via inhalation. The compounds are preferably supplied in finely divided form along with a surfactant and propellant. Typical percentages of active compound are 0.01%-20% by weight, preferably 1%-10%. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25%-5%. The balance of the composition is ordinarily propellant. A carrier can also be included as desired, e.g., lecithin for intranasal delivery. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Additionally, the compound or salt of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

It will be appreciated by one of ordinary skill in the art that, in addition to the aforedescribed pharmaceutical compositions, the compound or salt of the present invention may be formulated as inclusion complexes, such as cyclodextrin inclusion complexes, or liposomes. Liposomes serve to target the compounds to a particular tissue. Liposomes can also be used to increase the half-life of the inventive compound. Liposomes useful in the present invention include emulsions, foams, micelles, insoluble monolayers, liquid crystals, phospholipid dispersions, lamellar layers and the like. In these preparations, the active agent to be delivered is incorporated as part of a liposome, alone or in conjunction with a suitable chemotherapeutic agent. Thus, liposomes filled with a desired inventive compound or salt thereof, can be directed to the site of a specific tissue type, hepatic cells, for example, where the liposomes then deliver the selected compositions. Liposomes for use in the invention are formed from standard vesicle-forming lipids, which generally include neutral and negatively charged phospholipids and a sterol, such as cholesterol. The selection of lipids is generally guided by consideration of, for example, liposome size and stability of the liposomes in the blood stream. A variety of methods are available for preparing liposomes, as described in, for example, Szoka et al., *Ann. Rev. Biophys. Bioeng.,* 9, 467 (1980), and U.S. Pat. Nos. 4,235,871, 4,501,728, 4,837,028, and 5,019,369. For targeting to the cells of a particular tissue type, a ligand to be incorporated into the liposome can include, for example, antibodies or fragments thereof specific for cell surface determinants of the targeted tissue type. A liposome suspension containing a compound or salt of the present invention may be administered intravenously, locally, topically, etc. in a dose that varies according to the mode of administration, the agent being delivered, and the stage of disease being treated.

Suitable doses and dosage regimens can be determined by conventional range-finding techniques known to those of ordinary skill in the art. Generally, treatment is initiated with smaller dosages that are less than the optimum dose of the compound. Thereafter, the dosage is increased by small increments until the optimum effect under the circumstances is reached. The present inventive method typically will involve the administration of about 0.1 to about 300 mg of one or more of the compounds described above per kg body weight of the individual.

In some embodiments, a compound of the present invention is represented by Formula Ia:

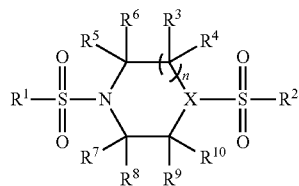

(Ia)

wherein n=1 to 3, $R^1$ and $R^2$ are aryl, phenyl, or heteroaryl, substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkyl, $C_6$-$C_{10}$ aryl, heteroaryl, heteroaryloxy, alkylenedioxy, $OR^4$, $SR^4$, $NR^4R^5$, $NCOR^4$, $OCOR^4$, $SCOR^4$, $SOR^4$, $SO_2R^4$, $SO_2NR^4R^5$, nitro, boronic acid, and halogen, $R^3$ and $R^4$ are independently selected from the group consisting of H, $C_1$-$C_{10}$ alkyl, $C_2$-$C_{10}$ cycloalkyl, $C_1$-$C_{10}$ alkynyl, $C_3$-$C_{10}$ cycloalkyl, $C_3$-$C_{10}$ cycloalkenyl, $COR^6$, F, and $CF_3$, or, taken together, form C=O, $R^5$ is H, $C_1$-$C_{10}$ alkyl, or F, $R^6$ to $R^{10}$ are H, and X is CH or N, or a pharmaceutically acceptable salt thereof.

In some embodiments, a compound of the present invention is represented by Formula II:

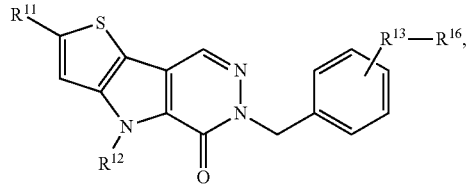

(II)

wherein:

$R^{11}$ is selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, $OR^{17}$, $SR^{17}$, $SOR^{17}$, $SO_2R^{17}$, $NR^{17}R^{18}$, $NCOR^{17}$, $SCOR^{17}$, $OCOR^{17}$, $B(OH)_2$, and halogen, $R^{12}$ is selected from the group consisting of $C_1$-$C_{10}$ alkyl, $C_3$-$C_{10}$ cycloalkyl, $NCOR^{17}$, and $SO_2R^{17}$, $R^{13}$ is selected from the group consisting of $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, heteroaryl, $OR^{17}$, $SR^{17}$, $NR^{17}R^{18}$, $NCOR^{17}$, $OCOR^{17}$, $SCOR^{17}$, $SOR^{17}$, $SO_2R^{17}$, $SO_2NR^{17}R^{18}$, $CF_3$, and halogen, and $R^{17}$ and $R^{18}$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, and $C_6$-$C_{10}$ aryl, or a pharmaceutically acceptable salt thereof.

One skilled in the art will appreciate that suitable methods of utilizing a compound and administering it to a human for the treatment of conditions or disease states responsive to activation of mutant PKRs (and/or PKR wild type), such as those diseases and conditions disclosed herein, are available. Although more than one route can be used to administer a particular compound, a particular route can provide a more immediate and more effective reaction than another route. Accordingly, the described methods are merely exemplary and are in no way limiting.

The dose administered to a human in accordance with the present invention should be sufficient to affect the desired response. Such responses include reversal or prevention of the bad effects of the disease responsive to activation of mutant PKR (and/or wild type PKR) for which treatment is desired or to elicit the desired benefit. One skilled in the art will recognize that dosage will depend upon a variety of factors, including the age, condition, and body weight of the human. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states may require prolonged treatment involving multiple administrations.

A compound described herein may be an activator of a PKR, for example, a wild type (wt) or mutated PKR (e.g., R510Q, R532W, OR T384W). Exemplary compounds are shown in Table 1. As shown in Table 1, A refers to a compound that has a % activation at 1 μM of from 1 to 100. B refers to an a compound that has a % activation at 1 μM of from 101 to 500. C refers a compound that has a % activation at 1 μM of >500.

In Table 1, a compound described herein may also have an AC50 of wild type PKR, PKR R532W, PKR T384W, PKR G332S, PKR G364D, PKR G37E and/or PKR R479H. AA refers to an AC50 less than 100 nM, BB refers to an AC50 from 101 nM to 500 nM and CC refers to an AC50 greater than 500 nM.

TABLE 1

| Structure | % Act. R510Q | % Act. R532W | % Act. T384W | % Act. WT | PKR WT AC50 (μM) | PKR R510Q AC50 (μM) | PKR R532W AC50 (μM) | PKR T384W AC50 (μM) |
|---|---|---|---|---|---|---|---|---|
| | B | A | A | B | | | | |
| | B | A | B | B | | | | |
| | B | B | B | B | | | | |
| | B | B | B | B | | | | |
| 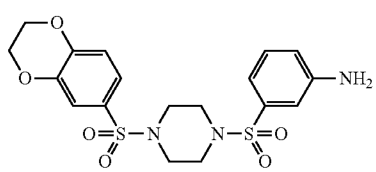 [SMILES: Nc1cccc(S(=O)(=O)N2CCN(S(=O)(=O)c3ccc4c(c3)OCCO4)CC2)c1] | A | B | A | A | | | | |
| | B | B | B | B | | | | |
| | B | B | B | B | | | | |
| | B | B | B | B | | | | |

TABLE 1-continued

| Structure | | | | | | | | |
|---|---|---|---|---|---|---|---|---|
| (methylsulfinyl-thienopyrrolopyridazinone with 3-methoxybenzyl) | B | B | A | A | AA | AA | AA | AA |
| (methylthio-thienopyrrolopyridazinone with 3-hydroxybenzyl) | C | B | B | B | AA | AA | AA | AA |
| (methyl-thienopyrrolopyridazinone with pentyl) | B | B | B | B | | | | |
| (methylsulfinyl-thienopyrrolopyridazinone with 3-aminobenzyl) | B | B | B | B | | AA | BB | AA |
| (methylsulfinyl-thienopyrrolopyridazinone with 2-fluorobenzyl) | B | B | B | B | BB | BB | CC | CC |
| (methylsulfinyl-thienopyrrolopyridazinone with 3-hydroxybenzyl) | B | B | B | B | AA | AA | AA | AA |

| Structure | PKR G332S AC50 (μM) | PKR G364D AC50 (μM) | PKR G37E AC50 (μM) | PKR R479H AC50 (μM) |
|---|---|---|---|---|

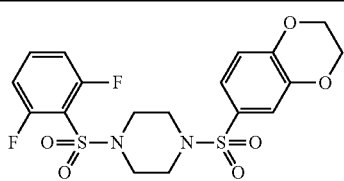

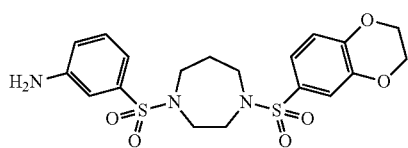 [SMILES: Nc1cccc(S(=O)(=O)N2CCCN(S(=O)(=O)c3ccc4c(c3)OCCO4)CC2)c1]

TABLE 1-continued
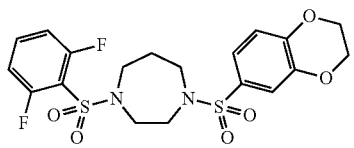 [SMILES: O=S(=O)(c1ccc2c(c1)OCCO2)N1CCCN(S(=O)(=O)c2c(F)cccc2F)CC1]
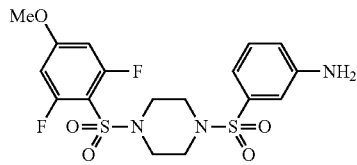 [SMILES: COc1cc(F)c(S(=O)(=O)N2CCN(S(=O)(=O)c3cccc(N)c3)CC2)c(F)c1]
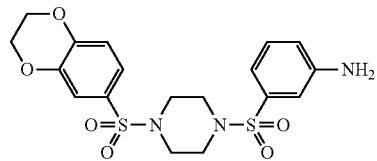 [SMILES: Nc1cccc(S(=O)(=O)N2CCN(S(=O)(=O)c3ccc4c(c3)OCCO4)CC2)c1]
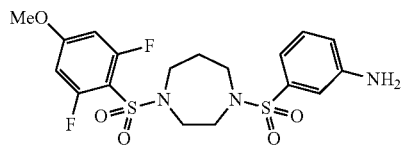 [SMILES: COc1cc(F)c(S(=O)(=O)N2CCCN(S(=O)(=O)c3cccc(N)c3)CC2)c(F)c1]
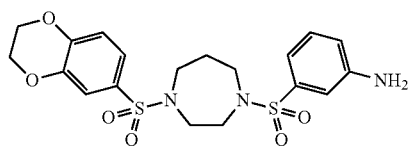 [SMILES: Nc1cccc(S(=O)(=O)N2CCCN(S(=O)(=O)c3ccc4c(c3)OCCO4)CC2)c1]
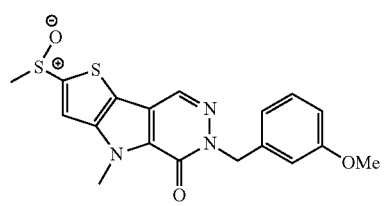 [SMILES: COc1cccc(Cn2ncc3c4sc([S+](C)[O-])cc4n(C)c3c2=O)c1]   AA   AA   AA
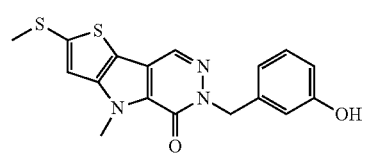 [SMILES: CSc1cc2c(s1)c1cnn(Cc3cccc(O)c3)c(=O)c1n2C]   AA   AA   AA
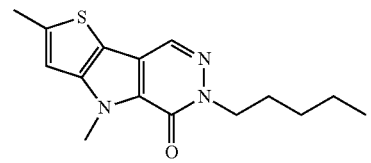 [SMILES: CCCCCn1ncc2c3sc(C)cc3n(C)c2c1=O]

| | | | | |
|---|---|---|---|---|
| (structure: methylsulfinyl-thienopyrrolopyridazinone with 3-aminobenzyl) | BB | AA | CC | AA |
| (structure: methylsulfinyl-thienopyrrolopyridazinone with 2-fluorobenzyl) | CC | BB | BB | |
| (structure: methylsulfinyl-thienopyrrolopyridazinone with 3-hydroxybenzyl) | AA | AA | AA | |

The compounds of the invention can prepared by any suitable method, such as those disclosed in the International Patent Application WO2010/042867, the content of which is hereby incorporated by reference. Examplary compounds of the present invention are:

1-(2,3-dihydrobenzo[b][1,4]dioxin-6-ylsulfonyl)-4-(4-methoxyphenylsulfonyl)piperazine (1).
1,4-bis(2,3-dihydrobenzo[b][1,4]dioxin-6-ylsulfonyl)piperazine (2).
1,4-bis(4-methoxyphenylsulfonyl)piperazine (3).
4-(4-(2,3 dihydrobenzo[b][1,4]dioxin-6-ylsulfonyl)piperazin-1ylsulfonyl) benzonitrile (4).
1-(4-chlorophenylsulfonyl)-4-(2,3-dihydrobenzo[b][1,4]dioxin-6-ylsulfonyl)piperazine (5).
1-(2,3-dihydrobenzo[b]I1,4]dioxin-6-ylsulfonyl)-4-(4-fluorophenylsulfonyl)piperazine (6).
1-(2,3-dihydrobenzo[b][1,4]dioxin-6-ylsulfonyl)-4-(3-fluorophenylsulfonyl)piperazine (7).
1-(2,3-dihydrobenzo[b][1,4]dioxin-6-ylsulfonyl)-4-(2-fluorophenylsulfonyl)piperazine (8).
1-(2,6-difluorophenylsulfonyl)-4-(2,3-dihydrobenzo[b][1,4]dioxin-6-ylsulfonyl)piperazine (9).
1-(2,3-dihydrobenzo[b][1,4]dioxin-6-ylsulfonyl)-4-(2,4,5-trifluorophenylsulfonyl)piperazine (10).
1-(2,6-difluoro-4-methoxyphenylsulfonyl)-4-(2,3-dihydrobenzo[b][1,4]dioxin-6-ylsulfonyl) piperazine (11).
1-(2,S-difluoro-4-propylphenylsulfonyl)-4-(2,3-dihydrobenzo[b][1,4]dioxin-6ylsulfonyl) piperazine (12).
3-(4-(2,3-dihydrobenzo[b][1,4]dioxin-6-ylsulfonyl)piperazin-1-ylsulfonyl)-2,4-difluorophenol (13).
1-(2,4-difluorophenylsulfonyl)-4-(2,3-dihydrobenzo[b][1,4]dioxin-6-ylsulfonyl)piperazine (14).
1-(2,3-dihydrobenzo[b][1,4]dioxin-6-ylsulfonyl)-4-(phenylsulfonyl)piperazine (15).
1-(2,3-dihydrobenzo[b][1,4]dioxin-6-ylsulfonyl)-4-(3)(trifluoromethyl)phenylsulfonyl) piperazine (16).
1-(2,3-dihydrobenzo[bJ[1,4]dioxin-6-ylsulfonyl)-4-(3-methoxyphenylsulfonyl)piperazine (17).
1-(2,3-dihydrobenzo[bJ[1,4Jdioxin-6-ylsulfonyl)-4-(pyridin-2-ylsulfonyl)piperazine (18).
2-(4-(2,3-dihydrobenzo[bJ[1,4Jdioxin-6-ylsulfonyl)piperazin-1-ylsulfonyl)pyridine L-oxide (19).
4-(2,6-difluorophenylsulfonyl)-1-(2,3-dihydrobenzo[bJ[1,4Jdioxin-6ylsulfonyl)piperidine (20).
1-(2,6-difluorophenylsulfonyl)-4-(4-methoxyphenylsulfonyl)piperazine (21).
1,4-bis(2,6-difluorophenylsulfonyl)piperazine (22).
1-(2,6-difluorophenylsulfonyl)-4-(3,4-dihydro-2H-benzo[b][1,4]dioxepin-7-ylsulfonyl) piperazine (23).
1-(benzo[d][1,3]dioxol-5-ylsulfonyl)-4-(2,6-difluorophenylsulfonyl)piperazine (24).
6-(4-(2,6-difluorophenylsulfonyl)piperazin-1-ylsulfonyl)-4-methyl-3,4-dihydro-2H-benzo[b][1,4]oxazine (25).
1-(2,6-difluorophenylsulfonyl)-4-(naphthalen-2-ylsulfonyl) piperazine (26).
1-(2,6-difluorophenylsulfonyl)-4-(2,2-dimethylchroman-6-ylsulfonyl)piperazine (27).
5-(4-(2,6-difluorophenylsulfonyl)piperazin-1-ylsulfonyl)-1-methyl-1H-indole (28).
5-(4-(2,6-difluorophenylsulfonyl)piperazin-1-ylsulfonyl)-2-methylbenzo[d]thiazole (29).
1-(2,6-difluorophenylsulfonyl)-4-(2,3-dihydrobenzo[b][1,4]dioxin-6-ylsulfonyl)piperidine (30).
1-(2,6-difluorophenylsulfonyl)-4-(2,3-dihydrobenzo[b][1,4]dioxin-6-ylsulfonyl)-1,4-diazepane (31).
N-(2-(2,6-difluorophenylsulfonamido)ethyl)-2,3-dihydrobenzo[b][1,4]dioxine-6-sulfonamide (32).
N-(3-(2,6-difluorophenylsulfonamido)propyl)-2,3-dihydrobenzo[b][1,4]dioxine-6-sulfonamide (33).
N-(4-(2,6-difluorophenylsulfonamido)butyl)-2,3-dihydrobenzo[b][1,4]dioxine-6-sulfonamide (34).
N-(5-(2,6-difluorophenylsulfonamido)pentyl)-2,3-dihydrobenzo[b][1,4]dioxine-6-sulfonamide (35).
N-(6-(2,6-difluorophenylsulfonamido)hexyl)-2,3-dihydrobenzo[b][1,4]dioxine-6-sulfonamide (36).
N-« trans)-4-(2,6-difluorophenylsulfonamido)cyC10hexyl)-2,3-dihydrobenzo[b][1,4]dioxine-6-sulfonamide (37).
N-« cis)-4-(2,6-difluorophenylsulfonamido)cyC10hexyl)-2,3-dihydrobenzo[b][1,4]dioxine-6-sulfonamide (38).

N-(1-(2,6-difluorophenylsulfonyl)piperidin-4-yl)-2,3-dihydrobenzo[b][1,4]dioxine-6-sulfonamide (39).
N-(1-(2,3-dihydrobenzo[b][1,4]dioxin-6-ylsulfonyl)piperidin-4-yl)-2,6-difluorobenzenesulfonamide (40).
N-(1-(2,6-difluorophenylsulfonyl)pyrrolidin-3-yl)-2,3-dihydrobenzo[b][1,4]dioxine-6-sulfonamide (41).
N-(1-(2,3-dihydrobenzo[b)[1,4]dioxin-6-ylsulfonyl)pyrrolidin-3-yl)-2,6-difluorobenzenesulfonamide (42).
N-((1-(2,6-difluorophenylsulfonyl)azetidin-3-yl)methyl)-2,3-dihydrobenzo[b][1,4]dioxine-6-sulfonamide (43).
N-((1-(2,3-dihydrobenzo[b) [1,4]dioxin-6-ylsulfonyl)azetidin-3-yl)methyl)-2,6-difluorobenzenesulfonamide (44).
(S)-4-(2,6-difluorophenylsulfonyl)-1-(2,3-dihydrobenzo[b][1,4]dioxin-6-ylsulfonyl)-2-methylpiperazine (45).
(R)-4-(2,6-difluorophenylsulfonyl)-1-(2,3-dihydrobenzo[b][1,4]dioxin-6-ylsulfonyl)-2-methylpiperazine (46).
(S)-1-(2,6-difluorophenylsulfonyl)-4-(2,3-dihydrobenzo[b][1,4]dioxin-6-ylsulfonyl)-2-methylpiperazine (48).
(R)-1-(2,6-difluorophenylsulfonyl)-4-(2,3-dihydrobenzo[b][1,4]dioxin-6-ylsulfonyl)-2-methylpiperazine (47).
4-(2,6-difluorophenylsulfonyl)-1-(2,3-dihydrobenzo[b][1,4]dioxin-6-ylsulfonyl)piperazin-2-one (49).
1-(2,6-difluorophenylsulfonyl)-4-(2,3-dihydrobenzo[b](1,4]dioxin-6-2-Bromo-4-methyl-6-[(2-fluorophenyl)methyl]-4H-thieno[3,2-b]pyrrole[3,2-d]pyridazinone (65).
2,4-Methyl-6-[(2-fluorophenyl)methyl]-4H-thieno[3,2-b]pyrrole[3,2-d]pyridazinone (66).
2-Vinyl-4-methyl-6-[(2-fluorophenyl)methyl]-4H-thieno[3,2-b]pyrrole[3,2-d]pyridazinone (67).
2-Ethyl-4-methyl-6-[(2-fluorophenyl)methyl]-4H-thieno[3,2-b]pyrrole[3,2-d]pyridazinone (68).
2-Isopropyl-4-methyl-6-[(2-fluorophenyl)methyl]-4H-thieno[3,2-b]pyrrole[3,2-d]pyridazinone (69).
4-Methyl-6-[(2-fluorophenyl)methyl]-4H-thieno[3,2-b]pyrrole[3,2-d]pyridazinone (70).
2-Methoxy-4-methyl-6-[(2-fluorophenyl)methyl]-4H-thieno[3,2-b]pyrrole[3,2-d]pyridazinone (71).
2-Methylthio-4-methyl-6-[(2-fluorophenyl)methyl]-4H-thieno[3,2-b]pyrrole[3,2-d]pyridazinone (72).
2-Methylsulfinyl-4-methyl-6-[(2-fluorophenyl)methyl]-4H-thieno[3,2-b]pyrrole[3,2-d]pyridazinone (73) and 2-Methylsulfonyl-4-methyl-6-[(2-fluorophenyl)methyl]-4H-thieno[3,2-b]pyrrole[3,2-d]pyridazinone (74).
Ethyl 6-formyl-2-nitro-4H-thieno[3,2-b]pyrrole-5-carboxylate (77).
2-Nitro-4-methyl-6-[(2-fluorophenyl)methyl]-4H-thieno[3,2-b]pyrrole[3,2-d]pyridazinone (80).
2-Acetylamido-4-methyl-6-[(2-fluorophenyl)methyl]-4H-thieno[3,2-b]pyrrole[3,2-d]-pyridazinone (81).
2-Cyano-4-methyl-6-[(2-fluorophenyl)methyl]-4H-thieno[3,2-b]pyrrole[3,2-d]pyridazinone (82).
Methyl-4-methyl-6-[(2-fluorophenyl)methyl]-4H-thieno[3,2-b]pyrrole[3,2-d]pyridazinone-2-carboxylate (83).
2-Formyl-4-methyl-6-[(2-fluorophenyl)methyl]-4H-thieno[3,2-b]pyrrole[3,2-d]pyridazinone (84).
2-Hydroxylmethyl-4-methyl-6-[(2-fluorophenyl)methyl]-4H-thieno[3,2-b]pyrrole[3,2-d]pyridazinone (85).
4-Methyl-6-[(2-fluorophenyl)methyl]-4H-thieno[3,2-b]pyrrole[3,2-d]pyridazinone, 2-ylboronic acid (86).
2-Acetyl-4-methyl-6-[(2-fluorophenyl)methyl]-4H-thieno[3,2-b]pyrrole[3,2-d]pyridazinone (87).
2-(2-hydroxylpropyl)-4-methyl-6-[(2-fluorophenyl)methyl]-4H-thieno[3,2-b]pyrrole-[3,2-d]pyridazinone (88).
2-Methyl-6-[(2-fluorophenyl)methyl]-4H-thieno[3,2-b]pyrrole[3,2-d]pyridazinone (89).
2-Methyl-4-ethyl-6-[(2-fluorophenyl)methyl]-4H-thieno[3,2-b]pyrrole[3,2-d]pyridazinone (90).
2-Methyl-4-isopropyl-6-[(2-fluorophenyl)methyl]-4H-thieno[3,2-b]pyrrole[3,2-d]pyridazinone (91)
2,4,8-Methyl-6-[(2-fluorophenyl)methyl]-4H-thieno[3,2-b]pyrrole[3,2-d]pyridazinone (92).
4-Methyl-4H-thieno[3,2-b]pyrrole[3,2-d]pyrimidinone (99).
4-Methyl-6-[(2-fluorophenyl)methyl]-4H-thieno[3,2-b]pyrrole[3,2-d]pyrimidinone (100).
2,4-Methyl-6-[(2-fluorophenyl)methyl]-4H-thieno[3,2-b]pyrrole[3,2-d]pyridazinone (101).
2,4-Methyl-6-pentyl-4H-thieno[3,2-b]pyrrole[3,2-d]pyridazinone (102).
2,4-Methyl-6-phenylmethyl-4H-thieno[3,2-b]pyrrole[3,2-d]pyridazinone (103).
2,4-Methyl-6-[3-fluorophenyl)methyl]-4H-thieno[3,2-b]pyrrole[3,2-d]pyridazinone (104).
2,4-Methyl-6-[(4-fluorophenyl)methyl]-4H-thieno[3,2-b]pyrrole[3,2-d]pyridazinone (105).
2,4-Methyl-6-[(2-chlorophenyl)methyl]-4H-thieno[3,2-b]pyrrole[3,2-d]pyridazinone (106).
2,4-Methyl-6-[(3-chlorophenyl)methyl]-4H-thieno[3,2-b]pyrrole[3,2-d]pyridazinone (107).
2,4-Methyl-6-[(4-chlorophenyl)methyl]-4H-thieno[3,2-b]pyrrole[3,2-d]pyridazinone (108).
2,4-Methyl-6-[(4-methylphenyl)methyl]-4H-thieno[3,2-b]pyrrole[3,2-d]pyridazinone (109).
2,4-Methyl-6-[(4-trifluoromethylphenyl)methyl]-4H-thieno[3,2-b]pyrrole[3,2-d]pyridazinone (110).
2,4-Methyl-6-[(4-methoxyphenyl)methyl]-4H-thieno[3,2-b]pyrrole[3,2-d]pyridazinone (111).
2,4-Methyl-6-[(2,4-difluorophenyl)methyl]-4H-thieno[3,2-b]pyrrole[3,2-d]pyridazinone (112).
2,4-Methyl-6-[(2,6-difluorophenyl)methyl]-4H-thieno[3,2-b]pyrrole[3,2-d]pyridazinone (113).
2,4-Methyl-6-[(2,3-difluorophenyl)methyl]-4H-thieno[3,2-b]pyrrole[3,2-d]pyridazinone (114).
2,4-Methyl-6-[{2-chloro-6-fluorophenyl)methyl]-4H-thieno[3,2-b]pyrrole[3,2-d]pyridazinone (115).
2,4-Methyl-6-[(2,3,4-trifluorophenyl)methyl]-4H-thieno[3,2-b]pyrrole[3,2-d]pyridazinone (116).
2,4-Methyl-6-[(2,3,5,6-tetrafluorophenyl)methyl]-4H-thieno[3,2-b]pyrrole[3,2-d]pyridazinone (117).
2,4-Methyl-6-[(3-methyl-2-fluorophenyl)methyl]-4H-thieno[3,2-b]pyrrole[3,2-d]pyridazinone (118).
2,4-Methyl-6-[(4-methyl-2,3-fluorophenyl)methyl]-4H-thieno[3,2-b]pyrrole[3,2-d]pyridazinone (119).
2,4-Methyl-6-[(2-fluoro-4-trifluoromethylphenyl)methyl]-4H-thieno[3,2-b]pyrrole[3,2-d]pyridazinone (120).
2,4-Methyl-6-[(3-fluoro-4-methoxyphenyl)methyl]-4H-thieno[3,2-b]pyrrole[3,2-d]pyridazinone (121).

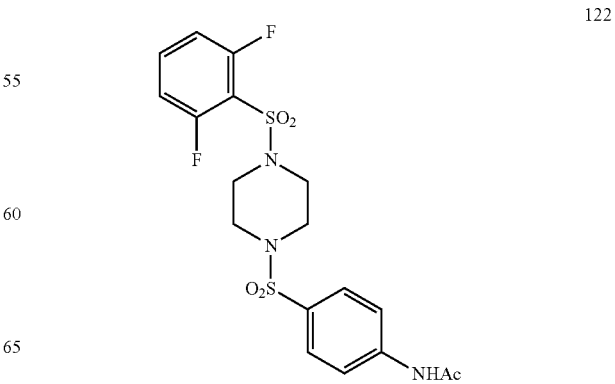

122

123
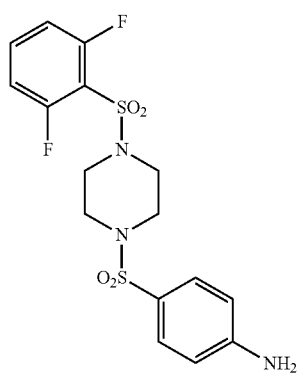
124
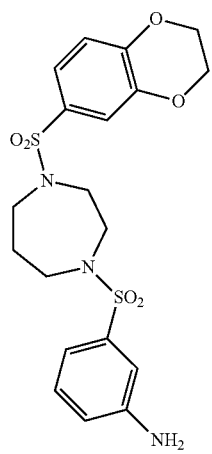
125
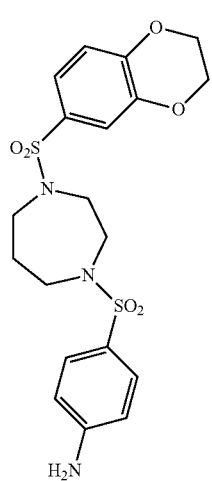
126
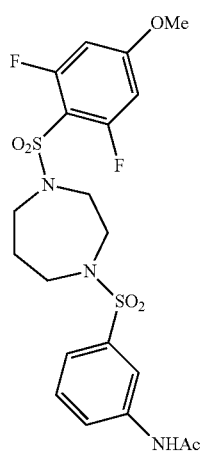
127
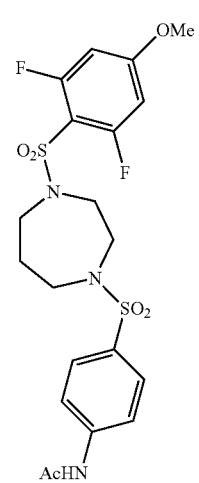
128
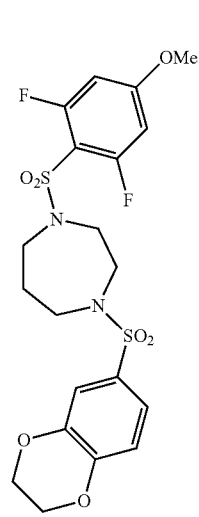

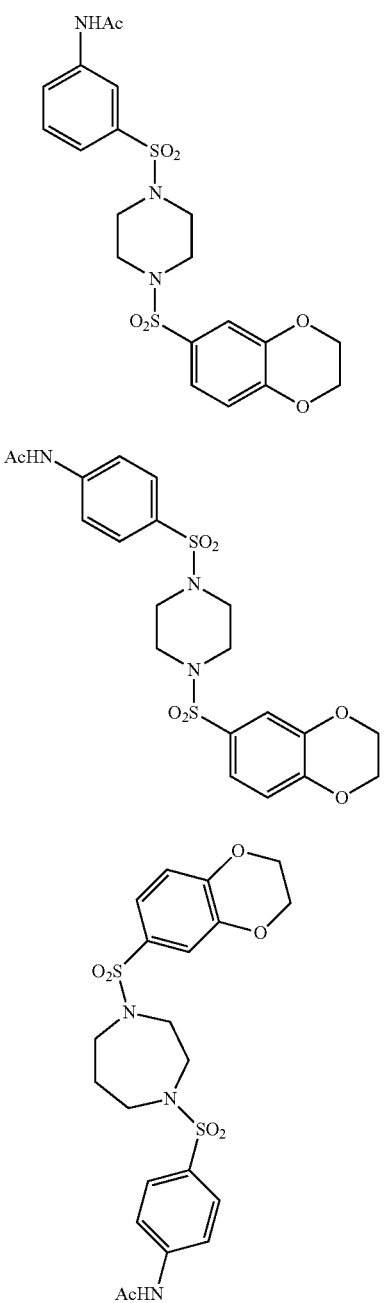

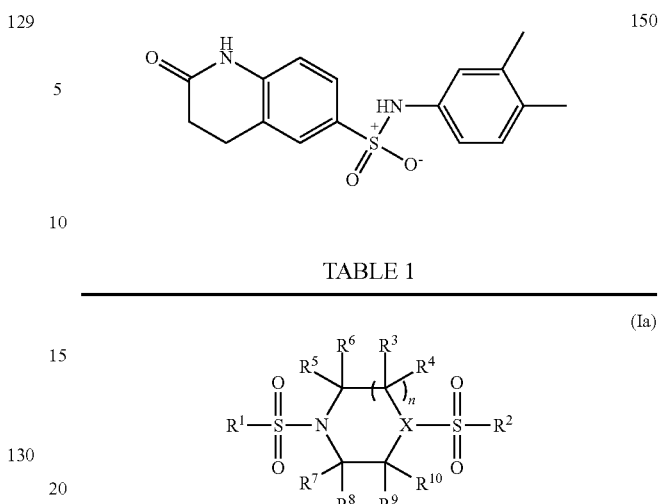

TABLE 1

(Ia)

| Compound No. | X | R¹ | R² |
|---|---|---|---|
| 133 | N | m-acetylaminophenyl | 2,6-difluoro-4-methoxyphenyl |
| 134 | N | m-aminophenyl | 2,6-difluoro-4-methoxyphenyl |
| 135 | N | m-aminophenyl | 6-(2,3-dihydro-benzo[b][1,4]dioxinyl) |
| 136 | N | m-(ethylamino)phenyl | 6-(2,3-dihydro-benzo[b][1,4]dioxinyl) |
| 137 | N | m-aminophenyl | 2,6-difluorophenyl |
| 138 | N | m-(N,N-dimethylamino)phenyl | 6-(2,3-dihydro-benzo[b][1,4]dioxinyl) |
| 139 | N | p-aminophenyl | 2,6-difluoro-4-methoxyphenyl |
| 140 | N | m-hydroxyphenyl | 2,6-difluorophenyl |
| 141* | N | m-aminophenyl | 2,6-difluoro-4-methoxyphenyl |
| 142 | N | m-(methylamino)phenyl | 6-(2,3-dihydro-benzo[b][1,4]dioxinyl) |
| 143* | N | p-aminophenyl | 2,6-difluoro-4-methoxyphenyl |
| 144 | N | 2,6-difluoro-4-methoxyphenyl | 2-thiophenyl |
| 145 | N | 2,6-difluoro-4-methoxyphenyl | 2-furanyl |
| 146 | N | 2-amino-4-pyridyl | 6-(2,3-dihydro-benzo[b][1,4]dioxinyl) |
| 151 | N | p-aminophenyl | 6-(2,3-dihydro-benzo[b][1,4]dioxinyl) |

*n = 2; others n = 1, R³-R¹⁰ = H.

TABLE 2

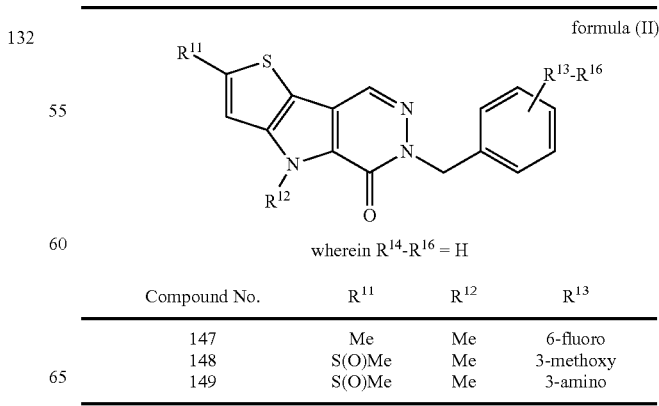

formula (II)

wherein $R^{14}$-$R^{16}$ = H

| Compound No. | R¹¹ | R¹² | R¹³ |
|---|---|---|---|
| 147 | Me | Me | 6-fluoro |
| 148 | S(O)Me | Me | 3-methoxy |
| 149 | S(O)Me | Me | 3-amino |

EXAMPLE 1

PKR Mutant Assay

Procedure:
  PKR or PKR mutant enzyme solution was diluted in assay buffer. 2 µL of test compound was added into wells first, and then 180 µL reaction mix was added.
  Reactions mixture with test compound was assembled except for ADP, and plates were stored for 60 minutes at room temperature.
  20 uL ADP was added to start reaction at room temperature and reaction progress was measured as changes in absorbance at 340 nm wavelength at room temperature.

Test Compound Preparation:
  Test compound stock was made at 100× concentration in 100% DMSO (10 mM)
  1 to 3 dilutions were made for 11 points (i.e. 50 µl of first concentration added to 100 µl 100% DMSO to yield 3.33 mM, 50 µl of this added to 100 µl DMSO to yield 1.11 mM, and so forth)
  1 to 100 dilution into assay (2 µl in 200 µl) yielded starting concentration of 100 µM, decreasing 3 fold for 11 points.

Assay Buffer: 100 mM KCl, 50 mM Tris 7.5, 5 mM $MgCl_2$, 1 mM DTT, 0.03% BSA

Reaction Mixture: PKR mutant enzyme: 80-400 ng/well; ADP: 0.22-1.65 mM; PEP: 0.1-0.5 mM; NADH: 180 uM; LDH: 0.5 units (Sigma#59023); DTT: 1 mM; BSA: 0.03%.

An exemplary compound was tested to be an activator of wild type PKR, PKRR532W, PKRR479H, and PKRG332S with an AC50 less than 100 nM against each wild type/mutant enzyme.

EXAMPLE 2

PKR WT Single Point Percent Activation Assay

A compound described herein was diluted with DMSO and tested at 1 µM concentration. The enzyme was diluted in 1× Buffer: (100 mM KCl, 50 mM Tris 7.5, 5 mM $MgCl_2$, 1 mM DTT, 0.03% BSA). 2 µL of compound solution was first added into wells, and then 180 µL of enzyme solution was added. Assays were assembled except for ADP, and plates were stored for 60 minutes at RT. 20 µL ADP was added to start the assay and assay output was evaluated using OD340 at SpectraMax. The assay was run at room temperature.
Final Concentration: PKR wt (100 ng/well), Tris pH 7.5 (50 mM), KCl (100 mM), $MgCl_2$ (5 mM), ADP (0.48 mM), PEP (0.15 mM), NADH (180 µM), LDH (0.5 units, Sigma 59023), DTT (1 mM) and BSA (0.03%).

EXAMPLE 3

PKR R510Q Single Point Percent Activation Assay

A compound described herein was diluted with DMSO and tested at 1 µM concentration. The enzyme was diluted in 1× Buffer: (100 mM KCl, 50 mM Tris 7.5, 5 mM $MgCl_2$, 1 mM DTT, 0.03% BSA). 2 µL of compound solution was first added into wells, and then 180 µL of enzyme solution was added. Assays were assembled except for ADP, and plates were stored for 60 minutes at RT. 20 µL ADP was added to start the assay and assay output was evaluated using OD340 at SpectraMax. The assay was run at room temperature.
Final Concentration: PKR R510Q (40 ng/well), Tris pH 7.5 (50 mM), KCl (100 mM), $MgCl_2$ (5 mM), ADP (0.2 mM), PEP (0.11 mM), NADH (180 µM), LDH (0.5 units, Sigma 59023), DTT (1 mM) and BSA (0.03%).

EXAMPLE 4

PKR R532W Single Point Percent Activation Assay

A compound described herein was diluted with DMSO and tested at 1 µM concentration. The enzyme was diluted in 1× Buffer: (100 mM KCl, 50 mM Tris 7.5, 5 mM $MgCl_2$, 1 mM DTT, 0.03% BSA). 2 µL of compound solution was first added into wells, and then 180 µL of enzyme solution was added. Assays were assembled except for ADP, and plates were stored for 60 minutes at RT. 20 µL ADP was added to start the assay and assay output was evaluated using OD340 at SpectraMax. The assay was run at room temperature.
Final Concentration: PKR R532W (100 ng/well), Tris pH 7.5 (50 mM), KCl (100 mM), MgCl2 (5 mM), ADP (0.36 mM), PEP (0.1 mM), NADH (180 µM), LDH (0.5 units, Sigma 59023), DTT (1 mM) and BSA (0.03%).

EXAMPLE 5

PKR T384W Single Point Percent Activation Assay

A compound described herein was diluted with DMSO and tested at 1 µM concentration. The enzyme was diluted in 1× Buffer: (100 mM KCl, 50 mM Tris 7.5, 5 mM $MgCl_2$, 1 mM DTT, 0.03% BSA). 2 µL of compound solution was first added into wells, and then 180 µL enzyme solution was added. Assays were assembled except for ADP, and plates were stored for 60 minutes at RT. 20 µL ADP was added to start the assay and assay output was evaluated using OD340 at SpectraMax. The assay was run at room temperature.
Final Concentration: PKR T384W soluble (300 ng/well), Tris pH 7.5 (50 mM), KCl (100 mM), MgCl2 (5 mM), ADP (0.08 mM), PEP (0.23 mM), NADH (180 µM), LDH (0.5 units, Sigma 59023), DTT (1 mM) and BSA (0.03%).

All references, including publications, patent applications, and patents, cited herein are hereby incorporated by reference to the same extent as if each reference were individually and specifically indicated to be incorporated by reference and were set forth in its entirety herein. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Variations of the disclosed embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for increasing the lifetime of red blood cells (RBCs) in need thereof comprising contacting blood an effective amount of (1) a compound of formula I, II, or III or a pharmaceutically acceptable salt thereof; (2) a composition comprising a compound of formula I, II, or III or a salt thereof, and a carrier or (3) a pharmaceutically acceptable composition comprising a compound of formula I, II, or III or a pharmaceutically acceptable salt thereof, and a pharmaceutically acceptable carrier, wherein:

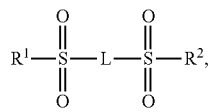
(I)

$R^1$ and $R^2$ are aryl or heteroaryl, optionally substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alklenedioxy, $OR^4$, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen, and
L is a linker comprising an amino group;
wherein:

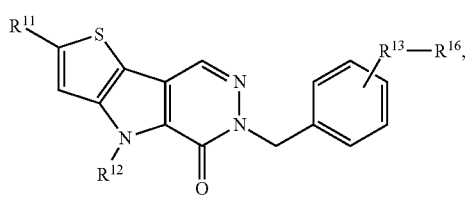
(II)

$R^{11}$ is selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, $OR^{17}$, $SR^{17}$, $SOR^{17}$, $SO_2R^{17}$, $NR^{17}R^{18}$, $NCOR^{17}$, $SCOR^{17}$, $COR^{17}$, $OCOR^{17}$, $B(OH)_2$, $NO_2$, $NHCOR^{17}$, CN, CHO, hydroxyl $C_1$-$C_{10}$ alkyl, and halogen,
$R^{12}$ is selected from the group consisting of H, $C_1$-$C_2$ alkyl, $C_3$-$C_{10}$ cycloalkyl, $NCOR^{14}$, and $SO_2R^{14}$,
$R^{13}$ to $R^{16}$ are selected from the group consisting of H, $C_1$-$C_{10}$ alkyl, halo $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, heteroaryl, $OR^{17}$, $SR^{17}$, $NR^{17}R^{18}$, $NCOR^{17}$, $OCOR^{17}$, $SCOR^{17}$, $SOR^{17}$, $SO_2R^{17}$, $SO_2NR^{17}R^{18}$, $CF_3$, and halogen, and $R^{17}$ and $R^{18}$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, and $C_6$-$C_{10}$ aryl;
wherein:

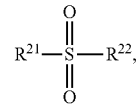
(III)

wherein $R^{21}$ and $R^{22}$ are aryl, substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alklenedioxy, $OR^{23}$, $SR^{23}$, $NR^{23}R^{24}$, $NCOR^{23}$, $OCOR^{23}$, $SCOR^{23}$, $SO_2R^{23}$, $SO_2NR^{23}R^{24}$, $NO_2$, $B(OH)_2$, CN and halogen,
wherein $R^{23}$ and $R^{24}$ are independently R, $C_1$-$C_{10}$ alkyl, F, $C_2$-$C_{10}$ alkenyl, $C_2$-$C_{10}$ alkynyl, $C_3$-$C_{10}$ cycloalkyl, $C_3$-$C_{10}$ cycloalkenyl, $COR^6$, and $CF_3$.

2. The method of claim 1, wherein the compound is added directly to whole blood or packed cells extracorporeally.

3. The method of claim 1, wherein the pharmaceutical composition is administered to a patient in need thereof.

4. A method for regulating 2,3-diphosphoglycerate levels in blood in need thereof comprising contacting blood with an effective amount of (1) a compound of formula I, II, or III or a pharmaceutically acceptable salt thereof; (2) a composition comprising a compound of formula I, II, or III or a salt thereof, and a carrier or (3) a pharmaceutically acceptable composition comprising a compound of formula I, II, or III or a pharmaceutically acceptable salt thereof, wherein:

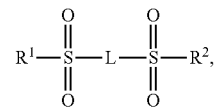
(I)

wherein $R^1$ and $R^2$ are aryl or heteroaryl, optionally substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alklenedioxy, $OR^4$, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen, and
L is a linker comprising an amino group;

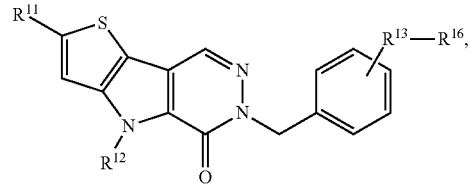
(II)

wherein:
- $R^{11}$ is selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, $OR^{17}$, $SR^{17}$, $SOR^{17}$, $SO_2R^{17}$, $NR^{17}R^{18}$, $NCOR^{17}$, $SCOR^{17}$, $COR^{17}$, $OCOR^{17}$, $B(OH)_2$, $NO_2$, $NHCOR^{17}$, CN, CHO, hydroxyl $C_1$-$C_{10}$ alkyl, and halogen,
- $R^{12}$ is selected from the group consisting of H, $C_1$-$C_2$ alkyl, $C_3$-$C_{10}$ cycloalkyl, $NCOR^{14}$, and $SO_2R^{14}$,
- $R^{13}$ to $R^{16}$ are selected from the group consisting of H, $C_1$-$C_{10}$ alkyl, halo $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, heteroaryl, $OR^{17}$, $SR^{17}$, $NR^{17}R^{18}$, $NCOR^{17}$, $OCOR^{17}$, $SCOR^{17}$, $SOR^{17}$, $SO_2R^{17}$, $SO_2NR^{17}R^{18}$, $CF_3$, and halogen, and
- $R^{17}$ and $R^{18}$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, and $C_6$-$C_{10}$ aryl;

wherein:

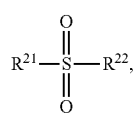
(III)

wherein $R^{21}$ and $R^{22}$ are aryl, substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$dihaloalkyl, $C_1$-$C_{10}$trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alklenedioxy, $OR^{23}$, $SR^{23}$, $NR^{23}R^{24}$, $NCOR^{23}$, $OCOR^{23}$, $SCOR^{23}$, $SO_2R^{23}$, $SO_2NR^{23}R^{24}$, $NO_2$, $B(OH)_2$, CN and halogen, wherein $R^{23}$ and $R^{24}$ are independently R, $C_1$-$C_{10}$ alkyl, F, $C_2$-$C_{10}$ alkenyl, $C_2$-$C_{10}$ alkynyl, $C_3$-$C_{10}$ cycloalkyl, $C_3$-$C_{10}$ cycloalkenyl, $COR^6$, and $CF_3$.

5. A method for treating sickle cell anemia comprising administering to a subject in need thereof a therapeutically effective amount of (1) a compound of formula I, II, or III or a pharmaceutically acceptable salt thereof; or (2) a pharmaceutically acceptable composition comprising a compound of formula I, II, or III or a pharmaceutically acceptable salt thereof, and a pharmaceutically acceptable carrier, wherein:

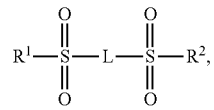
(I)

wherein $R^1$ and $R^2$ are aryl or heteroaryl, optionally substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alklenedioxy, $OR^4$, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen, and L is a linker comprising an amino group;

wherein:

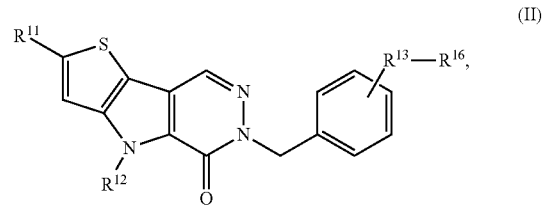
(II)

- $R^{11}$ is selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, $OR^{17}$, $SR^{17}$, $SOR^{17}$, $SO_2R^{17}$, $NR^{17}R^{18}$, $NCOR^{17}$, $SCOR^{17}$, $COR^{17}$, $OCOR^{17}$, $B(OH)_2$, $NO_2$, $NHCOR^{17}$, CN, CHO, hydroxyl $C_1$-$C_{10}$ alkyl, and halogen,
- $R^{12}$ is selected from the group consisting of H, $C_1$-$C_2$ alkyl, $C_3$-$C_{10}$ cycloalkyl, $NCOR^{14}$, and $SO_2R^{14}$,
- $R^{13}$ to $R^{16}$ are selected from the group consisting of H, $C_1$-$C_{10}$ alkyl, halo $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cyc; cycloalkenyl, $C_6$-$C_{10}$ aryl, heteroaryl, $OR^{17}$, $SR^{17}$, $NR^{17}R^{18}$, $NCOR^{17}$, $OCOR^{17}$, $SCOR^{17}$, $SOR^{17}$, $SO_2R^{17}$, $SO_2NR^{17}R^{18}$, $CF_3$, and halogen, and
- $R^{17}$ and $R^{18}$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, and $C_6$-$C_{10}$ aryl;

wherein:

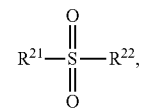
(III)

wherein $R^{21}$ and $R^{22}$ are aryl, substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$dihaloalkyl, $C_1$-$C_{10}$trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alklenedioxy, $OR^{23}$, $SR^{23}$, $NR^{23}R^{24}$, $NCOR^{23}$, $OCOR^{23}$, $SCOR^{23}$, $SO_2R^{23}$, $SO_2NR^{23}R^{24}$, $NO_2$, $B(OH)_2$, CN and halogen, wherein $R^{23}$ and $R^{24}$ are independently R, $C_1$-$C_{10}$ alkyl, F, $C_2$-$C_{10}$ alkenyl, $C_2$-$C_{10}$ alkynyl, $C_3$-$C_{10}$ cycloalkyl, $C_3$-$C_{10}$ cycloalkenyl, $COR^6$, and $CF_3$.

6. The method of claim 1, wherein the compound of formula (I) is a compound of formula (Ia):

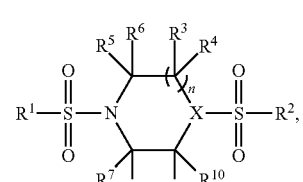
(Ia)

wherein n=1 to 3, $R^1$ and $R^2$ are aryl or heteroaryl, optionally substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alklenedioxy, $OR^4$, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen, $R^3$ and $R^4$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $COR^6$, F, and $CF_3$, or, $R^3$ and $R^4$, taken together, form C=O, $R^5$ and $R^7$ to $R^{10}$ are independently H, $C_1$-$C_{10}$ alkyl, or F, $R^6$ is $C_1$-$C_{10}$ alkyl or $C_3$-$C_{10}$ cycloalkyl, or each of $R^7$ and $R^8$ and of $R^9$ and $R^{10}$, together form C=O and X is CH or N, or a pharmaceutically acceptable salt thereof.

7. The method of claim 6, wherein $R^1$ and $R^2$ are phenyl substituted with one or more substituents selected from the group consisting of $C_1$-$C_{10}$ alkyl, $C_1$-$C_{10}$ trihaloalkyl, heterocyclyl, heteroaryl, alkylenedioxy, $OR^4$, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen, $R^3$ and $R^4$ are independently selected from the group consisting of H, $C_1$-$C_{10}$ alkyl, and F, or, taken together, form C=O, and $R^5$ and $R^7$ to $R^{10}$ are independently H, $C_1$-$C_{10}$ alkyl, or F.

8. The method of claim 6, wherein $R^1$ and $R^2$ are phenyl substituted with one or more substituents selected from the group consisting of $C_1$-$C_{10}$ alkyl, $C_1$-$C_{10}$ trihaloalkyl, heterocyclyl, heteroaryl, alklenedioxy, CN, and halogen, and $R^3$ to $R^{10}$ are H.

9. The method of claim 6, wherein X is N.

10. The method of claim 6, wherein n is 1.

11. The method of claim 1, wherein $R^1$ is selected from the group consisting of phenyl, 4-methylphenyl, 2-methylphenyl, 2fluorophenyl, 4-chlorophenyl, 4-fluorophenyl, 4,2-difluorophenyl, 2,6-difluorophenyl, 2,4,5trifluorophenyl, 4-chloro-2-fluorophenyl, 3-chloro-2-fluorophenyl, 4-trifluoromethylphenyl, 3-trifluoromethylphenyl, 2,6-difluoro-4-trifluoromethylphenyl, 2,6-difluoro-4methoxyphenyl, 2,5-difluoro-4-propylphenyl, 2,6-difluoro-3-hydroxyphenyl, 2,4difluorophenyl, 4-bromo-2-fluorophenyl, 2,6-difluoro-3-hydroxyphenyl, 3-methoxyphenyl, 4-methoxyphenyl, 4-cyanophenyl, 2-nitrophenyl, 2-pyridyl, 2-pyridyl-1-oxide, 2-(boronic acid)phenyl, 3-(boronic acid)phenyl, and 4-(boronic acid)phenyl.

12. The method of claim 1, wherein $R^1$ is selected from the group consisting of 2,6-difluoro-4-trifluoromethylphenyl, 2,6-difluorophenyl, 2,6-difluoro-4-methoxyphenyl, 2,6-difluoro-3-hydroxyphenyl, and 4-methoxyphenyl.

13. The method of claim 1, wherein $R^2$ is 6-(2,3-dihydrobenzo[b][1,4]dioxinyl), 7-(3,4-dihydro-2H-benzo[b][1,4]dioxepinyl), 5-benzo[d][1,4]dioxinyl, 7-(4-methyl-3,4-dihydro-2H-pyrido[3,2-b][1,4-oxazinyl), 2- naphthalenyl, 6-(2,2-dimethylchromanyl), 5-(1-methyl-1-H-indolyl), 6-(2-methylbenzo[d]thiazolyl), or 4-methoxyphenyl.

14. The method of claim 1, wherein $R^2$ is 6-(2,3-dihydrobenzo[b][1,4]dioxinyl).

15. The method of claim 6, wherein the compound is a compound of formula (Ia), X is N, n=1, and $R^3$ to $R^{10}$ is H, and $R^1$ and $R^2$ are as follows:

$R^1$ is 4-methoxyphenyl and R2 is 6-(2,3-dihydro-benzo[b][1,4]dioxinyl);

$R^1$ and $R^2$ are 6-(2,3-dihydro-benzo[b][1,4]dioxinyl);

$R^1$ and $R^2$ are 4-methoxyphenyl;

$R^1$ is 4-cyanophenyl and $R^2$ is 6-(2,3-dihydro-benzo[b][1,4]dioxinyl);

$R^1$ is 4-chlorophenyl and $R^2$ is 6-(2,3-dihydro-benzo[b][1,4]dioxinyl);

$R^1$ is 4-fluorophenyl and $R^2$ is 6-(2,3-dihydro-benzo[b][1,4]dioxinyl);

$R^1$ is 3-fluorophenyl and $R^2$ is 6-(2,3-dihydro-benzo[b][1,4]dioxinyl);

$R^1$ is 2-fluorophenyl and $R^2$ is 6-(2,3-dihydro-benzo[b][1,4]dioxinyl);

$R^1$ is 2,6-difluorophenyl and $R^2$ is 6-(2,3-dihydro-benzo[b][1,4]dioxinyl);

$R^1$ is 2,4,5-trifluorophenyl and $R^2$ is 6-(2,3-dihydro-benzo[b][1,4]dioxinyl);

$R^1$ is 2,6-difluoro-4-methoxyphenyl and $R^2$ is 6-(2,3-dihydro-benzo[b][1,4]dioxinyl);

$R^1$ is 2,5-difluoro-3-propylphenyl and $R^2$ is 6-(2,3-dihydro-benzo[b][1,4]dioxinyl);

$R^1$ is 2,6-difluoro-3-hydroxyphenyand $R^2$ is 6-(2,3-dihydro-benzo[b][1,4] dioxinyl);

$R^1$ is 2,4-difluorophenyl and $R^2$ is 6-(2,3-dihydro-benzo[b][1,4]dioxinyl);

$R^1$ is phenyl and $R^2$ is 6-(2,3-dihydro-benzo[b][1,4]dioxinyl);

$R^1$ is 3-(trifluoromethylphenyl) and $R^2$ is 6-(2,3-dihydro-benzo[b][1,4]dioinyl);

$R^1$ is 3-methoxyphenyl and $R^2$ is 6-(2,3-dihydro-benzo[b][1,4]dioxinyl);

$R^1$ is 4-methoxyphenyl and $R^2$ is 6-(2,3-dihydro-benzo[b][1,4]dioxinyl);

$R^1$ is 2-pyridyl and $R^2$ is 6-(2,3-dihydro-benzo[b][1,4]dioxinyl);

$R^1$ is 2-pyridyl-1-oxide and $R^2$ is 6-(2,3-dihydro-benzo[b][1,4]dioxinyl);

$R^1$ is 2,6-difluorophenyl and $R^2$ is 2,6-difluorophenyl;

$R^1$ is 2,6-difluorophenyl and $R^2$ is 7-(3,4-dihydro-2H-benzo[b][1,4]dioxepinyl);

$R^1$ is 2,6-difluorophenyl and $R^2$ is 5-benzo[d][1,4]dioxinyl;

$R^1$ is 2,6-difluorophenyl and $R^2$ is 7-(4-methyl-3,4-dihydro-2H-pyrido[3,2b-1,4]oxazinyl);

$R^1$ is 2,6-difluorophenyl and $R^2$ is 2-naphthalenyl;

$R^1$ is 2,6-difluorophenyl and $R^2$ is 6-(2,2-dimethylchromanyl);

$R^1$ is 2,6-difluorophenyl and $R^2$ is 5-(1-methyl-1H-indolyl);

$R^1$ is 2,6-difluorophenyl and $R^2$ is 6-(2-methylbenzo[d]thiazolyl); or $R^1$ is 2,6-difluorophenyl and $R^2$ is 6-(2,3-dihydrobenzo[b][1,4]dioinyl).

16. The method of claim 1, wherein the compound of formula (I) is a compound of formula (Ib):

(Ib)

17. The method of claim 16, wherein the compound is a compound of formula (Ic):

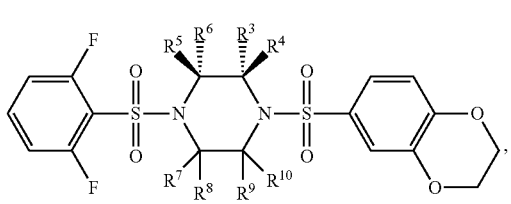
(Ic)

wherein $R^3$ to $R^{10}$ are H or methyl, $R^3$ to $R^6$ and $R^9$ and $R^{10}$ are H or methyl and $R^7$ form C=O, or $R^3$ to $R^8$ are H or methyl and $R^9$ and $R^{10}$ form C=O.

18. The method of claim 17, wherein (i) $R^5$ is methyl and $R^3$, $R^4$, and $R^6$ to $R^{10}$ are H; (ii) $R^6$ is methyl and $R^3$ to $R^5$ and $R^7$ to $R^{10}$ are H; (iii) $R^3$ is methyl and $R^4$ to $R^{10}$ are H; (iv) $R^4$ is methyl and $R^3$ and $R^5$ to $R^{10}$ are H; (v) $R^3$ to $R^8$ are H and $R^9$ and $R^{10}$ form C=O; or (vi) $R^3$ to $R^6$ and $R^7$ and $R^8$ are H and $R^7$ and $R^8$ form C=O.

19. The method of claim 1, wherein $R^1$ is selected from the group consisting of 2-pyridyl, 2-pyridyl-N-oxide, 3-pyridyl, 3-pyridyl-N-oxide, 4pyridyl, 4-pyridyl-N-oxide, 2-pyrimidinyl, 2-pyrimidinyl-N-oxide, 4-pyrimidinyl, 4pyrimidinyl-N-oxide, 5-pyrimidinyl, 5-pyrimidinyl-N-oxide, 2-pyrazinyl, and 2-pyrazinyl-Noxide.

20. The method of claim 1, wherein X is CH.

21. The method of claim 20, wherein n is 1.

22. The method of claim 21, wherein $R^3$, $R^4$, and $R^5$ are H.

23. The method of claim 20, wherein $R^1$ is selected from the group consisting of 4-methylphenyl, 2-methylphenyl, 2-fluorophenyl, 3fluorophenyl, 4,2-difluorophenyl, 2,6-difluorophenyl, 2,4,5-trifluorophenyl, 2,6-difluoro-4-trifluoromethylphenyl, 4-chloro-2-fluoro, 3-chloro-2-fluoro, 4-trifluoromethylphenyl, 4-bromo-2-fluorophenyl, 4-methoxyphenyl, and 2-nitrophenyl.

24. The method of claim 20, wherein $R^1$ is selected from the group consisting of 2,6-difluoro-4-trifluoromethylphenyl, 2,6 difluorophenyl, and 4-methoxyphenyl.

25. The method of claim 20, wherein $R^2$ is 3,4-ethylenedioxyphenyl.

26. The method of claim 1, wherein L is a linear group, cyclic group, or a combination thereof.

27. The method of claim 26, wherein L is an alkylene diamino, cycloalkylamino amino, or cycloalkylamino alkylamino.

28. The method of claim 27, wherein L is N,N'-(ethane-1,2-diyl), N,N'-(propane-1,3-diyl), N,N'-(butane-1,4-diyl), N,N'-(pentane-1,5-diyl), N,N'-(hexane-1,6-diyl), N,N'-((trans)-cyclohexane-1,4-diyl), N,N'-((cis)-cyclohexane-1,4-diyl),

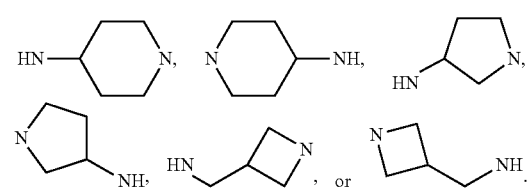

29. The method of claim 24, wherein $R^1$ is 2,6-difluorophenyl and $R^2$ is 6-(2,3-dihydrobenzo[b][1,4]dioxinyl).

30. The method of claim 1, wherein:
$R^{11}$ is selected from the group consisting of H, $C_1$-$C_{10}$ alkyl, $OR^{17}$, $SR^{17}$, $SOR^{17}$, $SO_2R^{17}$, $NR^{17}R^{18}$, $NCOR^{17}$, $SCOR^{17}$, $COR^{17}$, $OCOR^{17}$, $B(OH)_2$, $NO_2$, $NHCOR^{17}$, CN, CHO, hydroxy $C_1$-$C_{10}$ alkyl, and halogen,
$R^{12}$ is selected from the group consisting of H, methyl, $NCOR^{14}$, and $SO_2R^{14}$,
$R^{13}$ to $R^{16}$ are selected from the group consisting of H, $C_1$-$C_{10}$ alkyl, $OR^{17}$, $SR_{17}$, $NR^{17}R^{18}$, $NCOR^{17}$, $OCOR^{17}$, $SCOR^{17}$, $SOR^{17}$, $SO_2R^{17}$, $SO_2NR^{17}R^{18}CF_3$, and halogen, and
$R^{17}$ and $R^{18}$ are independently selected from the group consisting of H and $C_1$-$C_{10}$ alkyl.

31. The method of claim 30, wherein:
$R^{11}$ is selected from the group consisting of H, $C_1$-$C_{10}$ alkyl, $OR^{17}$, $SR^{17}$, $SOR^{17}$, $COR^{17}$, $OCOR^{17}$, $B(OH)_2$, $NO_2$, $NHCOR^{17}$, CN, CHO, hydroxy $C_1$-$C_{10}$ alkyl, and halogen,
$R^{12}$ is H or $C_1$-$C_2$ alkyl, and
$R^{13}$ to $R^{16}$ are selected from the group consisting of H, methyl, $CF_3$, methoxy, and halogen.

32. The method of claim 31, wherein:
$R^{11}$ is selected from the group consisting of H, methyl, ethyl, isopropyl, $OCH_3$, $SCH_3$, $S(O)CH_3$, $NO_2$, $NHCOCH_3$, CN, $COOCH_3$, CHO, $CH_2OH$, $B(OH)_2$, and $CH(OH)CH_3$,
$R^{12}$ is methyl,
$R^{13}$ is 2-fluoro or chloro, and
$R^{14}$ to $R^{16}$ are each H.

33. The method of claim 32, wherein:
$R^{11}$ and $R^{12}$ are methyl, $R^{13}$ is H, 2-fluoro, 3-fluoro, 4-fluoro, 2-chloro, 3-chloro, 4-chloro, 4-CF3, 4-methyl, or 4-methoxy, and $R^{14}$ to $R^{16}$ are H.

34. The method of claim 32, wherein $R^{11}$ and $R^{12}$ are methyl, and $R^{13}$ and $R^{14}$ are 2-fluoro and 4-fluoro, 2-fluoro and 6-fluoro, 2-fluoro and 3-fluoro, 2-choro and 6-fluoro, 2-fluoro and 3-methyl, 2-fluoro and 4-methyl, 2-fluoro and 4-$CF_3$, and 2-fluoro and 4-methoxy, and $R^{15}$ and $R^{16}$ are H.

35. The method of claim 32, wherein $R^{11}$ and $R^{12}$ are methyl, $R^{13}$ to $R^{15}$ are 2-fluoro, 3-fluoro, and 4-fluoro, and $R^{16}$ is H.

36. The method of claim 32, wherein $R^{11}$ and $R^{12}$ are methyl, $R^{13}$ to $R^{16}$ are 2-fluoro, 3-fluoro, 5-fluoro, and 6-fluoro.

37. The method of claim 1, wherein the compound of formula (I) is a compound of formula (Ia):

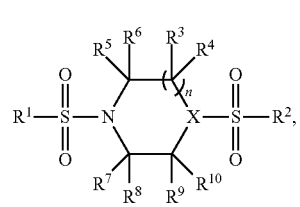
(Ia)

wherein n=1 to 3, and $R^2$ are aryl, phenyl, or heteroaryl, optionally substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ halo alkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alklenedioxy, $OR^4$, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen, $R^3$ and $R^4$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $COR^6$, F, and $CF_3$, or, $R^3$ and $R^4$, taken together, form C=O, $R^5$ and $R^7$ to $R^{10}$ are independently R, $C_1$-$C_{10}$ alkyl, or F, $R^6$ is $C_1$-$C_{10}$ alkyl or $C_3$-$C_{10}$ cycloalkyl, or each of $R^7$ and $R^8$ and of $R^9$ and $R^{10}$, together form C=O and X is CH or N.

38. A method for treating hemolytic anemia comprising administering to a subject in need thereof a therapeutically effective amount of (1) a compound of formula I, II, or III or a pharmaceutically acceptable salt thereof; or (2) a pharmaceutically acceptable composition comprising a compound of formula I, II, or III or a pharmaceutically acceptable salt thereof, and a pharmaceutically acceptable carrier, wherein:

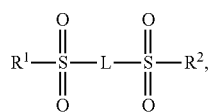
(I)

$R^1$ and $R^2$ are aryl or heteroaryl, optionally substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alklenedioxy, $OR^4$, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen, and L is a linker comprising an amino group;

wherein:

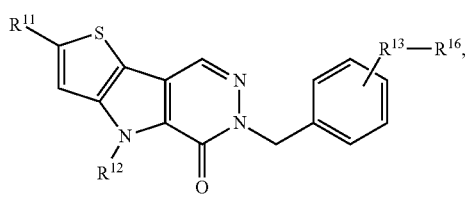
(II)

$R^{11}$ is selected from the group consisting of H, $C_1$-$C_{10}$ alkyl, $C_2$-$C_{10}$ alkenyl, $C_2$-$C_{10}$ alkynyl, $C_3$-$C_1$cycloalkyl, $C_3$-$C_{10}$ cycloalkenyl, $C_6$-$C_{10}$ aryl, $OR^{17}$, $SR^{17}$, $SOR^{17}$, $SO_2R^{17}$, $NR^{17}R^{18}$, $NCOR^{17}$, $SCOR^{17}$, $COR^{17}$, $OCOR^{17}$, $B(OH)_2$, $NO_2$, $NHCOR^{17}$, CN, CHO, hydroxyl $C_1$-$C_{10}$ alkyl, and halogen, $R^{12}$ is selected from the group consisting of H, $C_1$-$C_2$ alkyl, $C_3$-$C_{10}$ cycloalkyl, $NCOR^{14}$, and $SO_2R^{14}$, $R^{13}$ to $R^{16}$ are selected from the group consisting of H, $C_1$-$C_{10}$ alkyl, halo $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, heteroaryl, $OR^{17}$, $SR^{17}$, $NR^{17}R^{18}$, $NCOR^{17}$, $OCOR^{17}$, $SCOR^{17}$, $SOR^{17}$, $SO_2R^{17}$, $SO_2NR^{17}R^{18}$, $CF_3$, and halogen, and $R^{17}$ and $R^{18}$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, and $C_6$-$C_{10}$ aryl;

wherein:

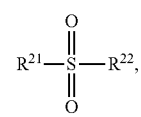
(III)

wherein $R^{21}$ and $R^{22}$ are aryl, substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alklenedioxy, $OR^{23}$, $SR^{23}$, $NR^{23}R^{24}$, $NCOR^{23}$, $OCOR^{23}$, $SCOR^{23}$, $SO_2R^{23}$, $SO_2NR^{23}R^{24}$, $NO_2$, $B(OH)_2$, CN and halogen, wherein $R^{23}$ and $R^{24}$ are independently R, $C_1$-$C_{10}$ alkyl, F, $C_2$-$C_{10}$ alkenyl, $C_2$-$C_{10}$ alkynyl, $C_3$-$C_{10}$ cycloalkyl, $C_3$-$C_{10}$ cycloalkenyl, $COR^6$, and $CF_3$.

39. The method of claim 38, wherein the hemolytic anemia is hereditary non-spherocytic hemolytic anemia.

40. A method of treating pyruvate kinase deficiency (PKD) in a subject comprising administering to a subject in need thereof a therapeutically effective amount of (1) a compound of formula I, II, or III or a pharmaceutically acceptable salt thereof; or (2) a pharmaceutically acceptable composition comprising a compound of formula I, II, or III or a pharmaceutically acceptable salt thereof, and a pharmaceutically acceptable carrier, wherein:

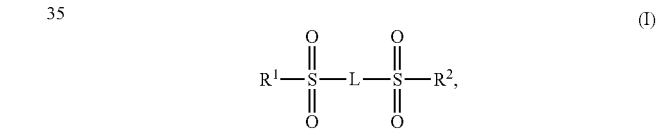
(I)

$R^1$ and $R^2$ are aryl or heteroaryl, opt10nally substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alklenedioxy, $OR^4$, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen, and L is a linker comprising an amino group;

wherein:

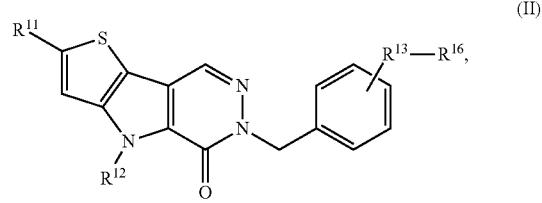
(II)

$R^{11}$ is selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, $OR^{17}$, SR$^{17}$, SOR$^{17}$, SO$_2$R$^{17}$, NR$^{17}$R$^{18}$, NCOR$^{17}$, SCOR$^{17}$, COR$^{17}$, OCOR$^{17}$, B(OH)$_2$, NO$_2$, NHCOR$^{17}$, CN, CHO, hydroxyl C$_1$-C$_{10}$ alkyl, and halogen, R$^{12}$ is selected from the group consisting of H, C$_1$-C$_2$ alkyl, C$_3$-C$_{10}$ cycloalkyl, NCOR$^{14}$, and SO$_2$R$^{14}$, R$^{13}$ to R$^{16}$ are selected from the group consisting of H, C$_1$-C$_{10}$ alkyl, halo C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkenyl, C$_6$-C$_{10}$ aryl, heteroaryl, OR$^{17}$, SR$^{17}$, NR$^{17}$R$^{18}$, NCOR$^{17}$, OCOR$^{17}$, SCOR$^{17}$, SOR$^{17}$, SO$_2$R$^{17}$, SO$_2$NR$^{17}$R$^{18}$, and halogen, and R$^{17}$ and R$^{18}$ are independently selected from the group consisting of H, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkenyl, and C$_6$-C$_{10}$ aryl;

wherein:

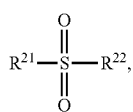
(III)

wherein R$^{21}$ and R$^{22}$ are aryl, substituted with one or more substituents selected from the group consisting of C$_1$-C$_{10}$ alkyl, C$_3$-C$_6$ alkylene, C$_2$-C$_{10}$ alkenyl, C$_2$-C$_{10}$ alkynyl, C$_1$-C$_{10}$ haloalkyl, C$_1$-C$_{10}$ dihaloalkyl, C$_1$-C$_{10}$ trihaloalkyl, C$_3$-C$_{10}$ cycloalkyl, C$_3$-C$_{10}$ cycloalkenyl, C$_6$-C$_{10}$ aryl, heterocyclyl, heteroaryl, heteroaryloxide, alklenedioxy, OR$^{23}$, SR$^{23}$, NR$^{23}$R$^{24}$, NCOR$^{23}$, OCOR$^{23}$, SCOR$^{23}$, SO$_2$R$^{23}$, SO$_2$NR$^{23}$R$^{24}$, NO$_2$, B(OH)$_2$, CN and halogen, wherein R$^{23}$ and R$^{24}$ are independently R, C$_1$-C$_{10}$ alkyl, F, C$_2$-C$_{10}$ alkenyl, C$_2$-C$_{10}$ alkynyl, C$_3$-C$_{10}$ cycloalkyl, C$_3$-C$_{10}$ cycloalkenyl, COR$^6$, and CF$_3$.

41. A method for activating PKR in red blood cells comprising administering to a subject in need thereof a therapeutically effective amount of (1) a compound of formula I, II, or III or a pharmaceutically acceptable salt thereof; or (2) a pharmaceutically acceptable composition comprising a compound of formula I, II, or III or a pharmaceutically acceptable salt thereof, and a pharmaceutically acceptable carrier, wherein:

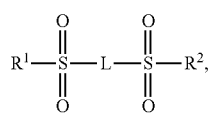
(I)

R$^1$ and R$^2$ are aryl or heteroaryl, opt10nally substituted with one or more substituents selected from the group consisting of C$_1$-C$_{10}$ alkyl, C$_3$-C$_6$ alkylene, C$_2$-C$_{10}$ alkenyl, C$_2$-C$_{10}$ alkynyl, C$_1$-C$_{10}$ haloalkyl, C$_1$-C$_{10}$ dihaloalkyl, C$_1$-C$_{10}$ trihaloalkyl, C$_3$-C$_{10}$ cycloalkyl, C$_3$-C$_{10}$ cycloalkenyl, C$_6$-C$_{10}$ aryl, heterocyclyl, heteroaryl, heteroaryloxide, alklenedioxy, OR$^4$, SR$^4$, NR$^4$R$^5$, NCOR$^4$, OCOR$^4$, SCOR$^4$, SOR$^4$, SO$_2$R$^4$, SO$_2$NR$^4$R$^5$, NO$_2$, B(OH)$_2$, CN, and halogen, and L is a linker comprising an amino group;

wherein:

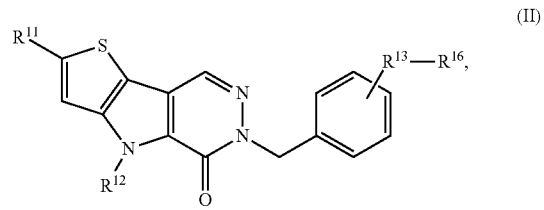
(II)

R$^{11}$ is selected from the group consisting of H, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkenyl, C$_6$-C$_{10}$ aryl, OR$^{17}$, SR$^{17}$, SOR$^{17}$, SO$_2$R$^{17}$, NR$^{17}$R$^{18}$, NCOR$^{17}$, SCOR$^{17}$, COR$^{17}$, OCOR$^{17}$, B(OH)$_2$, NO$_2$, NHCOR$^{17}$, CN, CHO, hydroxyl C$_1$-C$_{10}$ alkyl, and halogen, R$^{12}$ is selected from the group consisting of H, C$_1$-C$_2$ alkyl, C$_3$-C$_{10}$ cycloalkyl, NCOR$^{14}$, and SO$_2$R$^{14}$, R$^{13}$ to R$^{16}$ are selected from the group consisting of H, C$_1$-C$_{10}$ alkyl, halo C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkenyl, C$_6$-C$_{10}$ aryl, heteroaryl, OR$^{17}$, SR$^{17}$, NR$^{17}$R$^{18}$, NCOR$^{17}$, OCOR$^{17}$, SCOR$^{17}$, SOR$^{17}$, SO$_2$R$^{17}$, SO$_2$NR$^{17}$R$^{18}$, CF$_3$, and halogen, and R$^{17}$ and R$^{18}$ are independently selected from the group consisting of H, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkenyl, and C$_6$-C$_{10}$ aryl;

wherein:

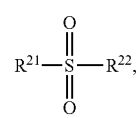
(III)

wherein R$^{21}$ and R$^{22}$ are aryl, substituted with one or more substituents selected from the group consisting of C$_1$-C$_{10}$ alkyl, C$_3$-C$_6$ alkylene, C$_2$-C$_{10}$ alkenyl, C$_2$-C$_{10}$ alkynyl, C$_1$-C$_{10}$ haloalkyl, C$_1$-C$_{10}$ dihaloalkyl, C$_1$-C$_{10}$ trihaloalkyl, C$_3$-C$_{10}$ cycloalkyl, C$_3$-C$_{10}$ cycloalkenyl, C$_6$-C$_{10}$ aryl, heterocyclyl, heteroaryl, heteroaryloxide, alklenedioxy, OR$^{23}$, SR$^{23}$, NR$^{23}$R$^{24}$, NCOR$^{23}$, OCOR$^{23}$, SCOR$^{23}$, SO$_2$R$^{23}$, SO$_2$NR$^{23}$R$^{24}$, NO$_2$, B(OH)$_2$, CN and halogen, wherein R$^{23}$ and R$^{24}$ are independently R, C$_1$-C$_{10}$ alkyl, F, C$_2$-C$_{10}$ alkenyl, C$_2$-C$_{10}$ alkynyl, C$_3$-C$_{10}$ cycloalkyl, C$_3$-C$_{10}$ cycloalkenyl, COR$^6$, and CF$_3$.

42. A method for treating thalassemia; hereditary spherocytosis; hereditary elliptocytosis; abetalipoproteinemia; Bassen-Kornzweig syndrome; paroxysmal nocturnal hemoglobinuria; acquired hemolytic anemia; or anemia of chronic diseases comprising administering to a subject in need thereof a therapeutically effective amount of (1) a compound of formula I, II, or III or a pharmaceutically acceptable salt thereof; or (2) a pharmaceutically acceptable composition comprising a compound of formula I, II, or III or a pharmaceutically acceptable salt thereof, and a pharmaceutically acceptable carrier, wherein:

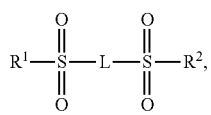

(I)

$R^1$ and $R^2$ are aryl or heteroaryl, optionally substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alklenedioxy, OR4, $SR^4$, $NR^4R^5$, $NCOR^4$, $OCOR^4$, $SCOR^4$, $SOR^4$, $SO_2R^4$, $SO_2NR^4R^5$, $NO_2$, $B(OH)_2$, CN, and halogen, and L is a linker comprising an amino group;
wherein:

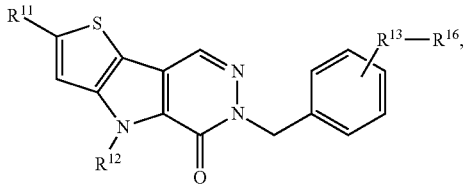

(II)

$R^{11}$ is selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, $OR^{17}$, $SR^{17}$, $SOR^{17}$, $SO_2R^{17}$, $NR^{17}R^{18}$, $NCOR^{17}$, $SCOR^{17}$, $COR^{17}$, $OCOR^{17}$, $B(OH)_2$, $NO_2$, $NHCOR^{17}$, CN, CHO, hydroxyl $C_1$-$C_{10}$ alkyl, and halogen, $R^{12}$ is selected from the group consisting of H, $C_1$-$C_2$ alkyl, $C_3$-$C_{10}$ cycloalkyl, $NCOR^{14}$, and $SO_2R^{14}$, $R^{13}$ to $R^{16}$ are selected from the group consisting of H, $C_1$-$C_{10}$ alkyl, halo $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_6$-$C_{10}$ aryl, heteroaryl, $OR^{17}$, $SR^{17}$, $NR^{17}R^{18}$, $NCOR^{17}$, $OCOR^{17}$, $SCOR^{17}$, $SOR^{17}$, $SO_2R^{17}$, $SO_2NR^{17}R^{18}$, $CF_3$, and halogen, and $R^{17}$ and $R^{18}$ are independently selected from the group consisting of H, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, and $C_6$-$C_{10}$ aryl;
wherein:

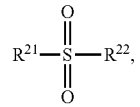

(III)

wherein $R^{21}$ and $R^{22}$ are aryl, substituted with one or more substituents selected from the group consisting of $C_1$-$C_{10}$ alkyl, $C_3$-$C_6$ alkylene, $C_2$-$C_{10}$ alkenyl, $C_2$-$C_{10}$ alkynyl, $C_1$-$C_{10}$ haloalkyl, $C_1$-$C_{10}$ dihaloalkyl, $C_1$-$C_{10}$ trihaloalkyl, $C_3$-$C_{10}$ cycloalkyl, $C_3$-$C_{10}$ cycloalkenyl, $C_6$-$C_{10}$ aryl, heterocyclyl, heteroaryl, heteroaryloxide, alklenedioxy, $OR^{23}$, $SR^{23}$, $NR^{23}R^{24}$, $NCOR^{23}$, $OCOR^{23}$, $SCOR^{23}$, $SO_2R^{23}$, $SO_2NR^{23}R^{24}$, $NO_2$, $B(OH)_2$, CN and halogen, wherein $R^{23}$ and $R^{24}$ are independently R, $C_1$-$C_{10}$ alkyl, F, $C_2$-$C_{10}$ alkenyl, $C_2$-$C_{10}$ alkynyl, $C_3$-$C_{10}$ cycloalkyl, $C_3$-$C_{10}$ cycloalkenyl, $COR^6$, and $CF_3$.

* * * * *